(12) United States Patent
Ghosh et al.

(10) Patent No.: US 11,077,191 B2
(45) Date of Patent: Aug. 3, 2021

(54) MULTIMODAL THERAPY FOR CANCER CELL DESTRUCTION

(71) Applicant: Southeast Missouri State University, Cape Girardeau, MO (US)

(72) Inventors: Santaneel Ghosh, Cape Girardeau, MO (US); Somesree GhoshMitra, Cape Girardeau, MO (US)

(73) Assignee: Southeast Missouri State University, Cape Girardeau, MO (US)

( * ) Notice: Subject to any disclaimer, the term of this patent is extended or adjusted under 35 U.S.C. 154(b) by 1214 days.

(21) Appl. No.: 15/279,726

(22) Filed: Sep. 29, 2016

(65) Prior Publication Data

US 2017/0128573 A1 May 11, 2017

Related U.S. Application Data

(60) Provisional application No. 62/235,850, filed on Oct. 1, 2015.

(51) Int. Cl.
*A61K 41/00* (2020.01)
*A61K 33/24* (2019.01)
*A61K 47/69* (2017.01)

(52) U.S. Cl.
CPC .......... *A61K 41/0052* (2013.01); *A61K 33/24* (2013.01); *A61K 41/0028* (2013.01); *A61K 47/6923* (2017.08); *A61K 47/6933* (2017.08); *A61K 47/6935* (2017.08)

(58) Field of Classification Search
CPC .......... A61N 1/406; A61N 2/008; A61N 5/04; A61N 5/10; A61N 5/062; A61K 47/64
See application file for complete search history.

(56) References Cited

U.S. PATENT DOCUMENTS

| 7,951,061 | B2 * | 5/2011 | Foreman | A61N 2/02 600/9 |
|---|---|---|---|---|
| 2005/0089993 | A1 | 4/2005 | Boccazzi et al. | |
| 2005/0090732 | A1 * | 4/2005 | Ivkov | A61N 1/406 600/411 |
| 2006/0099146 | A1 * | 5/2006 | Chow | A61K 9/5115 424/9.6 |
| 2014/0243733 | A1 | 8/2014 | McKenna et al. | |

OTHER PUBLICATIONS

Adams et al., "Increasing magnetite contents of polymeric magnetic particles dramatically improves labeling of neural stem cell transplant populations," Nanomedicine Nanotechnology, Biology and Medicine, 2015, vol. 11, pp. 19-29.

Alkilany et al., "Gold nanorods: Their potential for photothermal therapeutics and drug delivery, tempered by the complexity of their biological interactions," Advanced Drug Delivery Reviews, 2011, pp. 1-10.

Fortin et al., Size-sorted anionic iron oxide nanomagnets as colloidal mediators for magnetic hyperthermia, J. Am. Chem. Soc., 2007, vol. 129, pp. 2628-2635.

(Continued)

*Primary Examiner* — Samuel G Gilbert
(74) *Attorney, Agent, or Firm* — Armstrong Teasdale LLP

(57) ABSTRACT

The field of the disclosure relates generally to cancer cell destruction and, more specifically, to cancer cell destruction by photo-magnetic irradiation mediated multimodal therapy using smart nanostructures.

11 Claims, 13 Drawing Sheets

(56) References Cited

OTHER PUBLICATIONS

Ghosh et al., "Alternating Magnetic Field Controlled, Multifunctional Nano-Reservoirs: Intracellular Uptake and Improved Biocompatibility," Nanoscale Res. Lett., 2010, vol. 5, 10 pages.

Ghoshmitra et al., "Excellent biocompatibility of semiconductor quantum dots encased in multifunctional poly (N-isopropylacrylamide) nanoreservoirs and nuclear specific labeling of growing neurons," Applied Physics Letters, 2011, vol. 98, 103702.

Ghoshmitra et al., "Role of Engineered nanocarriers of axon regeneration and guidance: Current status and future trends," Advanced Drug Delivery Reviews, 2012, vol. 64, pp. 110-125.

Ghoshmitra et al., "Moderate Level Exposure to Magnetic Nanodots Encased in Tunable Poly(ethylene glycol) Analouge Biopolymer Shell Do Not Deleteriously Affect Neurite Outgrowth," Journal of Nanoscience and Nanotechnology, 2013, vol. 13, pp. 1-8.

Giuliani et al., "Low infra red laser light irradiation on cultured neural cells: effects on mitochondria and cell viability after oxidative stress," BMC Complementary and Alternative Medicine, 2009, vol. 9, No. 8, 10 pages.

Higuchi et al., "Visible light regulates neurite outgrowth of nerve cells," Cytotechnology, 2007, vol. 54, pp. 181-188.

Kim et al., "Enhancement of neurite outgrowth in PC12 cells by iron oxide nanoparticles," Biomaterials, 2011, vol. 32, pp. 2871-2877.

Kumar et al., "Magnetic Nanomaterials for Hyperthermia-based Therapy and Controlled Drug Delivery," Advanced Drug Delivery Reviews, 2011, 20 pages.

McCallister et al., "Engineered, thermoresponsive, magnetic nanocarriers of oligo (ethylene glycol)-methacrylate-based biopolymers," Applied Physics Express, 2014, vol. 7, 117003.

Purushotham et al., "Thermoresponsive magnetic composite nanomaterials for multimodal cancer therapy," Acta Biomaterialia, 2010, vol. 6, pp. 502-510.

Setua et al., "Cisplatin-tethered gold nanospheres for multimodal chemo-radiotherapy of glioblastoma," Nanoscale, 2014, vol. 6, pp. 10865-10873.

Di Corato et al., "Combining Magnetic Hyperthermia and Photodynamic Therapy for Tumor Ablation with Photoresponsive Magnetic Liposomes", ACS NANO, 2015, vol. 9, No. 3, pp. 2904-2916.

Jaque et al., "Nanoparticles for photothermal therapies", Nanoscale, 2014, vol. 6, pp. 9494-9530.

\* cited by examiner

MULTIMODAL THERAPY FOR CANCER CELL DESTRUCTION

CROSS-REFERENCE TO RELATED APPLICATION

This application claims priority to U.S. Provisional Application Ser. No. 62/235,850, filed Oct. 1, 2015, which is incorporated herein in its entirety.

FIELD OF THE DISCLOSURE

The field of the disclosure relates generally to cancer cell destruction and, more specifically, to cancer cell destruction by photo-magnetic irradiation mediated multimodal therapy using smart nanostructures.

BACKGROUND OF THE DISCLOSURE

Neuroblastoma is a childhood cancer which is diagnosed at a median age of 17 months, with an incidence rate of 10.2 per million children fewer than 15 years of age. There are about seven hundred new cases each year in the United States and in two out of three cases the disease is usually spread to the lymph nodes or other part of the body at the time of diagnosis. This is an embryonal tumor of the autonomic nervous systems, and it is the most common extra cranial tumor of childhood with long-term survival rates of only about 15%. Theoretically, tumors can appear anywhere along the sympathetic nervous system but in reality the majority of the tumors are detected in the adrenal medulla. Other sites for tumor include upper chest, neck and paraspinal spaces. Often, metastasis is seen in regional lymph nodes and to the bone marrow, and during advanced stages of the disease it can infiltrate a local organ such as a celiac axis tumor. Overexpression and dominance of cell survival pathways are mainly responsible for malignant transformation and metastasis of neural crest derived cells. Factors which define specific cases of neuroblastoma include stage, age, MYCN oncogene amplification, chromosome 11 q status, metastasis, histologic category and DNA ploidy.

Due to the biological heterogeneity of neuroblast tumors, different therapeutic strategies have been pursued. While reduced intensity therapeutic approaches, for example, surgery alone or in combination with moderate intensity chemotherapy, are the usual line of treatment for less aggressive tumors, high intensity chemo-radiotherapies are usually favored for tumors with more aggressive features. For high-risk neuroblastoma, treatment has been divided into three phases: (1) induction of remission, (2) consolidation of remission; and, (3) maintenance. Most commonly used induction regimens include cycles of cisplatin and etoposide as well as alternate uses of vincristine, doxorubicin, and cyclophosphamide. Additionally, two types of radiation therapies have been used: (1) external beam radiation therapy; and, (2) metaiodobenzylguanidine (MIBG) radiotherapy. Myeloablative chemotherapy with autologous hematopoietic stem-cell rescue and isotretinoin with anti-GD2 immunotherapy have also been considered for high risk neuroblastoma treatment.

Although the use of high intensity chemo-radiotherapies has demonstrated modest improvement in the treatment of high-risk neuroblastoma, undesirable side effects have occurred, including mouth sores, nausea, hair loss, and, most importantly, increased chance of infection. In addition to these, there may be several drug specific side effects, for example, cisplatin and carboplatin can affect kidneys, doxorubicin is a cardiotoxic agent, and cyclophosphamide can damage the bladder, ovaries and testicles, which in the future may affect fertility. Short-term side effects of radiation therapy include nausea, diarrhea, burn, and fatigue; while long-term side effects may lead to damage in DNA, which has a risk of developing into a second cancer many years after completion of radiotherapy. Unfortunately, despite implementing all advanced treatment modalities, 50-60% of patients in high risk groups have a relapse, and there is no known curative treatment available to date. Use of an anti-GD2 monoclonal antibody to prevent relapse is a good example of an immunotherapeutic approach to lessen the side effects of chemo, as well as radiotherapies. Future trends are to develop antibody-based treatment guidelines as well as a synergistic combination therapy.

Innovative approaches of the present disclosure include novel therapeutic implementation in order to overcome the existing challenges to treat high-risk neuroblastoma. An innovative technique that holds promise in the area of cancer diagnosis and therapeutics to perform precise drug delivery, multimodal therapy, and detection of circulating or residual cancer cells (all of which can play crucial roles in the treatment of high risk neuroblastoma) is the development of novel nanostructures coupled with smart actuation strategies. Nanostructured materials and smart surfaces carry excellent treatment potential for development of novel clinical solutions because they can be designed to target/detect specific cancer cells and be remotely tuned to release measured doses of therapeutic agents, which, in turn, may improve treatment efficacy, decrease therapy time, and decrease the quantities of the therapeutic agent necessary for effective treatment by 10-50 fold. In order to meet these goals cumulatively, "combinatorial therapeutics" approaches consisting of various nanostructures and advanced instrumentation are becoming one of the most exciting forefront fields. Oscillating magnetic field induced hyperthermia or photothermal destruction of cancer cells are among the most promising approaches. However, both fall short of addressing several concerns, including the use of high intensity magnetic or optical irradiation coupled with lower yield at clinically viable dose-levels. Rapid emergence of treatment resistance is a formidable challenge that needs a multimodal treatment approach, and, unfortunately, the aforementioned approaches do not address this concern.

Therefore, the goal of enhancing the treatment efficacy by combining a group of smart nanostructures, each of which are capable of performing a specific task with a novel strategy that has been unexplored thus far—is simultaneous photo-magnetic actuation. In some embodiments, three different types of nanostructures are used to accomplish the objectives: (1) core-shell magnetic nanospheres (CSMNSs), (b) polyvinylpyrrolidone (PVP) capped gold nanoparticles (AuNPs), and (c) cisplatin loaded thermo-responsive nanoparticles (CPNPs). The two protagonists (i.e., the CSMNS and the AuNPs) induce a coupled hyperthermia and oxidative stress under the hybrid photo-magnetic irradiation, whereas the CPNPs cause sustained release of the imbibed cisplatin during treatment. This results in enhanced synergy between the cisplatin and the photo-magnetic hyperthermia mediated cytotoxicity at a relatively lower irradiation and nanoparticle exposure level, as well as induced oxidative stress mediated apoptosis leading to complete ablation of the B35 neuroblastoma cells in culture. Additionally, by using this technique, exposures to the high energy x-rays have been avoided. The present disclosure shows that smart nanostructure-based photo-magnetic hybrid irradiation can remotely guide neuroblastoma cell destruction, which is an efficient technique in clinical management post modification. The present disclosure is further modified and extended to treat other aggressive cancers.

BRIEF DESCRIPTION OF THE DISCLOSURE

In one embodiment of the present disclosure, a multimodal method of cancer cell destruction is disclosed. The method comprises optically irradiating at least one nanostructure; and, simultaneously applying an oscillating magnetic field to the at least one nanostructure, wherein the nanostructure comprises at least one particle selected from the group consisting of a core-shell magnetic nanosphere and a capped gold nanoparticle; and, inducing a coupled hyperthermia and oxidative stress to at least one cancer cell through the simultaneous optical irradiation and oscillating magnetic field application to the nanostructure to destroy the cell.

In another embodiment of the present disclosure, a nanostructure for cancer cell destruction is disclosed. The nanostructure comprises at least one nanoparticle selected from the group consisting of a core-shell magnetic nanosphere, a capped gold nanoparticle, and a thermo-responsive nanoparticle comprising cisplatin.

In yet another embodiment of the present disclosure, a multimodal method of cancer cell destruction is disclosed. The method comprises optically irradiating at least one nanostructure; simultaneously applying an oscillating magnetic field to the at least one nanostructure, wherein the nanostructure comprises at least one thermo-responsive nanoparticle comprising cisplatin, wherein the simultaneous optical irradiation and oscillating magnetic field application creates a sustained release of the cisplatin from the nanoparticle; and, interacting the released cisplatin with at least one cancer cell to destroy the cell.

DETAILED DESCRIPTION OF THE DISCLOSURE

Figure 1A:
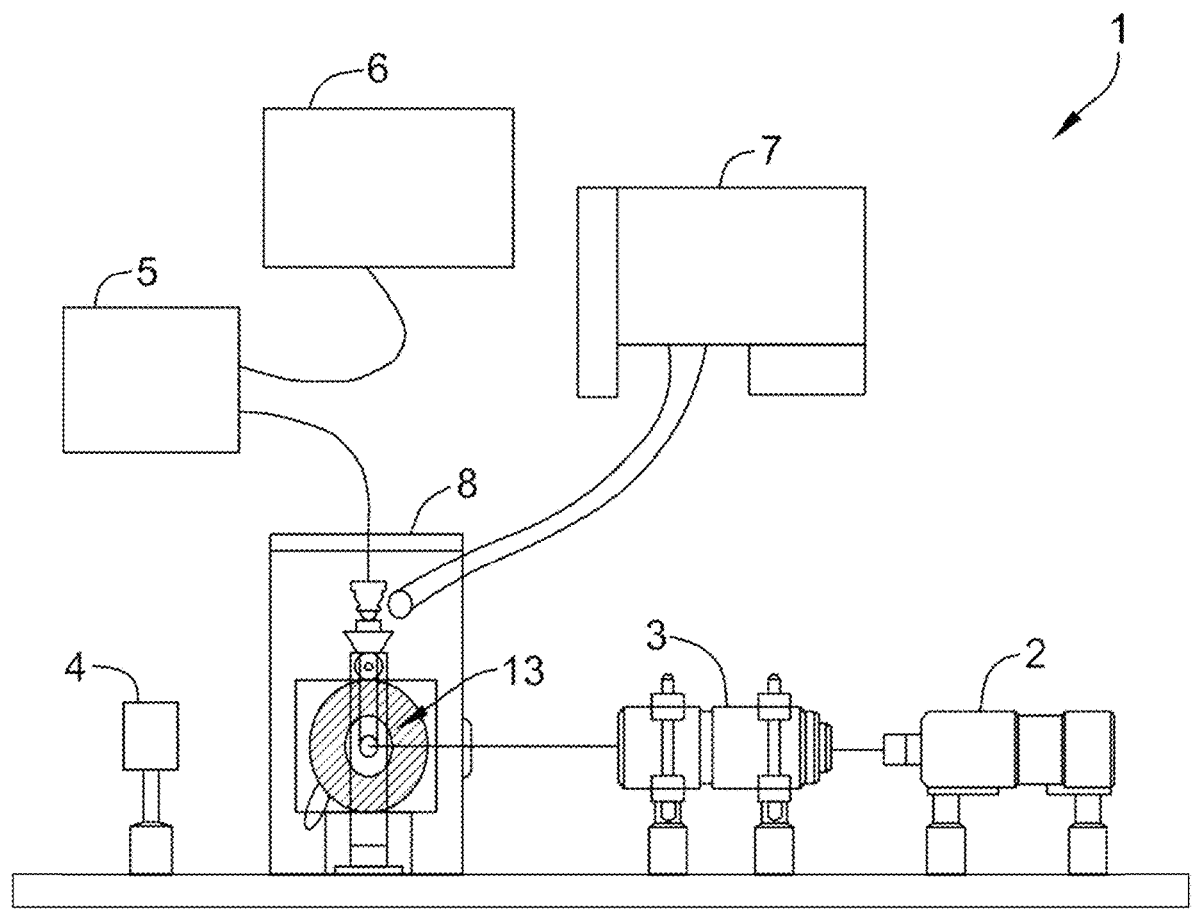
FIG. 1A is an exemplary embodiment of a system for generating combinations of magnetic and optical stimulation in accordance with the present disclosure.
Figure 1B:
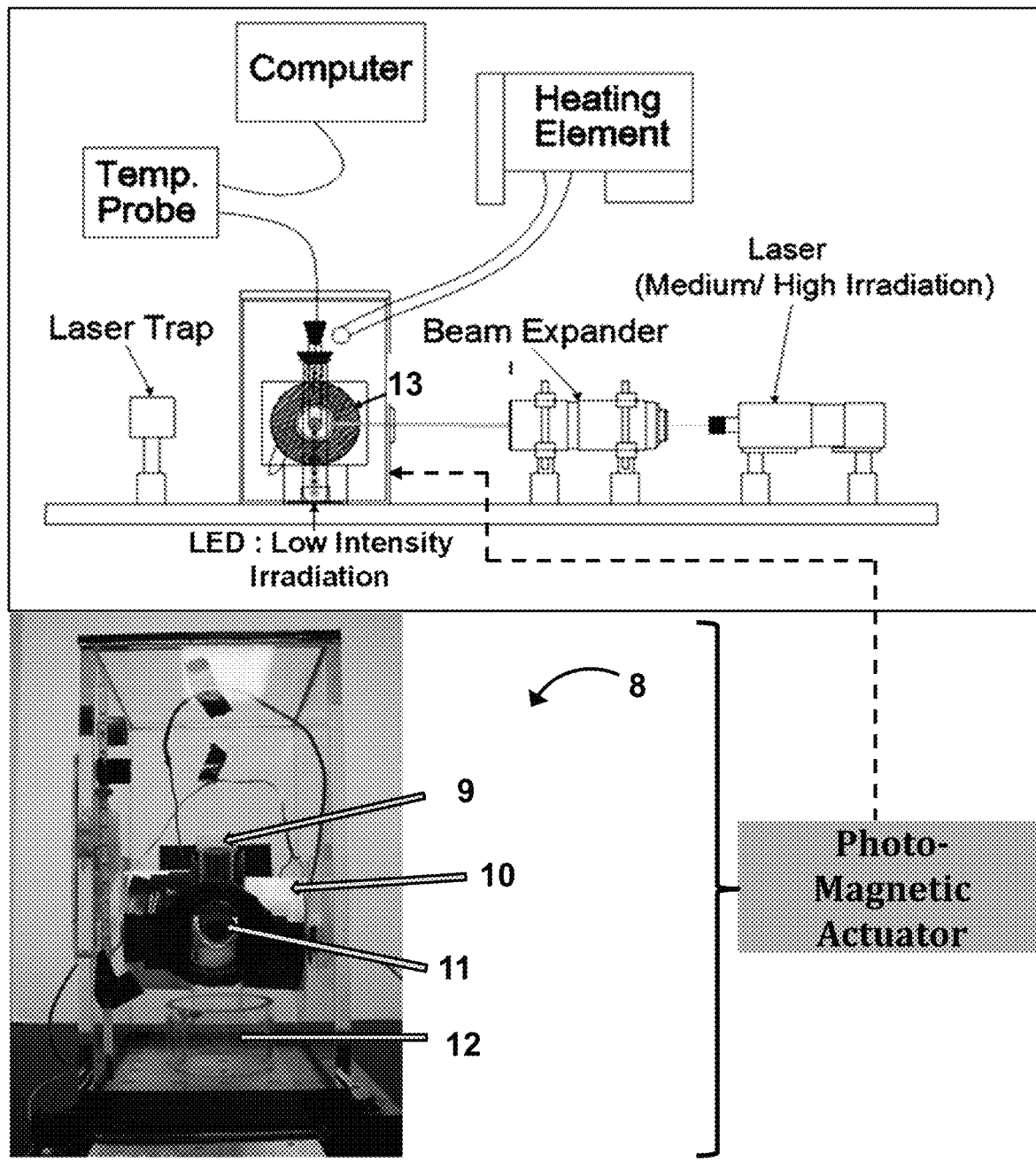
FIG. 1B is an exemplary embodiment of a device for combined optical-AC magnetic field irradiation of nanocarriers and B35 neuroblastoma cells including various components of an incubator, with a TPP tissue culture tube mounted inside in accordance with the present disclosure.

The present disclosure is directed to the simultaneous optical and AC magnetic field assisted therapeutic strategy for the destruction of aggressive cancer cells. FIG. 1A is an exemplary embodiment of a system 1 for generating combinations of magnetic and optical stimulation in accordance with the present disclosure. System 1 comprises a laser 2, a beam expander 3, a laser stop 4, a temperature probe 5, a computer 6, a heating element 7, and an incubator-actuator device 8. The device 8 comprises an AC/DC magnetic field generator 13. FIG. 1B is an exemplary embodiment of incubator-actuator device 8, as a component of system 1, in accordance with the present disclosure. The incubator-actuator device 8 comprises a sample chamber 9, an AC/DC magnetic field generating coil 10, a laser irradiation path 11, and an LED placement cage 12.

The sample chamber holds tissue culture tubes. Inside the sample chamber, in some embodiments, B35 neuroblastoma cells/PC12 cells are cultured and/or nano-carriers are colloidally dispersed. In some embodiments, the glass window is a high performance glass window located at a front wall of the device for transmitting the laser irradiation during moderate/high level optical stimulation.

In some embodiments, a circuit is used and the circuit utilizes a capacitor bank in series with an inductor coil and a 0.5 ohm resistor. The magnetic field is modified by changing the capacitor and/or the coil inductance.

The device further comprises a top and a bottom panel that are removable, which allows the samples within the chamber to be switched. In some embodiments, the device is attached to a base of the laser. In some embodiments, black absorbent tape material is used to confine the laser exposure to specific areas. In some embodiments, the electronics and the laser system are mounted at a distance from the incubator to prevent and/or mitigate potential interferences that create fluctuations of the magnetic field intensity during measurements.

In accordance with the present disclosure, in some embodiments, the beam expander expands the beam diameter that is directly coming from the laser (to minimize damage from laser irradiation), the laser produces optical excitation to the target(s) (e.g., AuNPs) for remote heating, the function generator generates different types of electrical waveforms over a wide range of frequencies, the computer records sample (nanocarrier or mammalian cell culture media) temperature responses during optical-AC magnetic field combined (or separate) actuation, as well as reading other responses, for example—light intensity, temperature inside the incubator during experiment, etc; and, the oscilloscope displays and analyzes the waveform of electronic signals.

In operation, the laser exposes a target to optical irradiation. The target can be, for example, a mammalian cell and/or a nanostructure. In some embodiments, the laser travels through a beam expander. In some embodiments, after travelling through the beam expander and irradiating the target, the laser hits a laser stop, which prevents the laser from further moving.

In some embodiments of the present disclosure, the optical irradiation is selected from the group consisting of LED-induced optical irradiation, ultraviolet-visible-induced optical irradiation, near infra-red (NIR)-induced optical irradiation, and combinations thereof. In some embodiments, the optical irradiation has an intensity of less than about 2 mW/cm2. In other embodiments, the optical irradiation has an intensity of from about 0 mW/cm2 to about 1,000 mW/cm2, or from about 2 mW/cm2 to about 1,000 mW/cm2. In some embodiments, the optical irradiation occurs at a wavelength between about 450 nm to about 675 nm, between about 450 nm to about 500 nm, or between about 620 nm to about 660 nm.

The optical irradiation range can be altered by a user by selecting a less or more powerful light irradiation source. For LED irradiation, in some embodiments, the range is increased by order of magnitude (e.g., at least up to 20 mW/cm2) by reducing the distance between the LED source and the sample chamber.

FIGS. 1A and 1B are exemplary embodiments of a setup for combined optical-AC magnetic field irradiation of nanocarriers and B35 neuroblastoma cells including various components of an incubator, with a TPP tissue culture tube mounted inside. This innovative setup enables high risk neuroblastoma cell exposure to a varying combination of optical and magnetic field excitation in the presence of specifically designed nanocarriers, thereby augmenting the positive outcomes of separate actuation strategies and the nanocarrier functionalities. In some embodiments, the field strength generated by the coils 10 (~150 Oe) is approximately 200 times weaker than that produced by an MIll machine (~3×10$^4$ Oe), which are known to be safe for use by people with medical implants such as pacemakers. A Helmholtz coil based design was adopted for conducting experimentation with animal models, if required, and to obtain a deeper penetration, a near infrared laser (NIR) can be used in accordance with the present disclosure. In some embodiments, for low-level photo-magnetic therapy, LED irradiation is used.

In some embodiments of the present disclosure, through the simultaneous optical irradiation and application of an oscillating magnetic field to a nanostructure, cancer cells are destroyed through the induction of a coupled hyperthermia and oxidative stress to the cancer cell. In some embodiments, the nanostructure comprises at least one particle selected from the group consisting of a CSMNS particle and a PVP capped gold nanoparticle. The CSMNS particles are nanoparticles. In some embodiments, magnetic nanoparticles (MNP) comprise the core of the core-shell CSMNS.

In some embodiments of the present disclosure, the nanostructure is part of a cluster of smart nanostructures that can be used for cell destruction, such as cancer cell destruction. Thus, in accordance with the present disclosure, the nanostructure can be a single nanostructure, multiple nanostructures, and/or a cluster of nanostructures.

In some embodiments of the present disclosure, the CSMNS particles have a diameter of from about 50 nm to about 400 nm, from about 100 nm to about 350 nm, or from about 240 nm to about 300 nm.

In some embodiments of the present disclosure, the nanostructure(s) comprise at least one CSMNS particle at a concentration of from about 50 μg/mL to about 600 μg/mL, from about 100 μg/mL to about 500 μg/mL, from about 200 μg/mL to about 600 μg/mL, or from about 200 μg/mL to about 400 μg/mL.

In some embodiments, the CSMNS particles comprise magnetic nanoparticles (MNPs). In some embodiments, the CSMNS particles comprise at least one of magnetite ($Fe_3O_4$), ferric oxide (e.g., γ-ferric oxide), maghemite, gadolinium-doped cobalt ferrite and combinations thereof.

In some embodiments, the shell comprises PVP and the at least one nanoparticle comprises gold. In some embodiments, the shell has a thickness of from about 2 nm to about 200 nm, from about 5 nm to about 50 nm, from about 40 nm to about 150 nm, or from about 2 nm to about 10 nm.

In some embodiments, the shell encapsulates a single nanoparticle or multiple nanoparticles. In some embodiments, the at least one nanoparticle has a size of from about 5 nm to about 100 nm, or from about 8 nm to about 20 nm. In some embodiments, the at least one nanoparticle has a diameter of from about 5 nm to about 270 nm, from about 5 nm to about 10 nm, or from about 210 nm to about 270 nm.

In some embodiments of the present disclosure, the shell has at least one additive loaded or attached thereon. In some embodiments, the at least one additive is a drug molecule. In some embodiments, the nanostructures release a therapeutic agent, and methods disclosed herein include measuring a release profile of a therapeutic agent from the nanostructures. The methods also further include characterizing a nanostructure response to the simultaneous optical irradiation and magnetic field radiation. The methods disclosed herein further include quantifying a nanostructure response to the simultaneous optical irradiation and oscillating magnetic field radiation.

In some embodiments, a PEG analogue based core-shell magnetic nano-reservoir system is disclosed. The system is based on ferromagnetic nanoparticles encapsulated within a thermo-activated polymer network that is non-toxic, anti-immunogenic and possesses a higher Young's modulus than other polymer networks, such as, for example, a poly(N-isopropylacrylamide)(PNIPAM) network system. The polymeric shell acts as a reservoir, for example, for drug molecules, while the magnetic core is a nano-source of heat. Thus, the release of imbibed drug molecules is initiated from the tunable excipient by causing volumetric shrinkage of the polymer network when exposed to the oscillating magnetic field.

In some embodiments, to generate the simultaneous optical stimulation, colloidally stable gold nanoparticles (AuNPs) having a particle size of from about 10 nm to about 50 nm, from about 15 nm to about 35 nm, about 10 nm, or about 20 nm are used. These AuNPs are selected with absorption peaks near about 520 nm. The incubator-actuator device of the present disclosure generates an alternating magnetic field with varying intensity and frequency range and optical irradiation into the target cell culture media when the power source is switched on.

The relaxation losses of the thermos-responsive core-shell nanostructures are then quantified. Field and frequency dependent temperature modulation of the target cells demonstrated the loss mechanism primarily related to the Brown relaxation. In some embodiments, optically induced losses from the gold nanoparticles were precisely regulated using a nanoparticle concentration of from about 2 μg/mL to about 10 μg/mL, or about 6 μg/mL in the culture media. As a result, magnetic and optical induced heating were performed using the same device inside the reaction vessel. For these excitations, temperature changes ranging from about 1° C. to about 5° C., or about 3° C. were achieved, and the temperatures were regulated within about 1° C. by modulating magnetic field, frequency and/or optical irradiation. The ability to induce controlled localized magnetic and optical actuation while allowing sustained release of therapeutic agents from the nanocarriers makes this system attractive for various biomedical applications, especially for tumor regression, wound healing or neuronal regeneration therapy.

In some embodiments of the present disclosure, the simultaneous optical irradiation and magnetic field radiation has a therapeutic application to the target, such as, for example, a mammalian cell. In some embodiments, the therapeutic application to the target is selected from the group consisting of tissue repair, wound healing, neural regeneration, neural circuit reconstruction, destroying cancer cells, regulating cell proliferation, regulating cell differentiation, tumor regression, facilitating neurite outgrowth of nerve cells, repairing endothelial cells, release profile of a drug, and combinations thereof.

In some embodiments, the following therapeutic applications and approaches are disclosed: combined (optical and AC magnetic field) hyperthermia at low, moderate, and high intensities for cancer cells; low level photo-magnetic exposure (therapy) for wound healing applications; low level photo-magnetic stimulation (to facilitate neurite outgrowth) of nerve cells; photo-magnetic exposure (i.e., nano-scale photo-magnetic energy exposure) of damaged endothelial cells; characterizing and quantifying the responses (e.g., specific absorption rate or SAR) of magnetic or optically responsive nanostructures exposed to simultaneous optical and oscillating magnetic field excitations; release profile of various drugs (for example—cancer drugs for chemotherapy, therapeutic proteins) that are loaded inside the polymeric nanoparticles or other smart nanostructures; and combinations thereof.

The types of mammalian cells that can be used for various experiments include (but are not limited to) the following: various cancer cells, model neuronal cells, such as, for example, PC12 and various primary neurons, endothelial cells, and fibroblasts, etc.

In some embodiments of the present disclosure, the nanostructure(s) comprise at least one AuNP particle at a concentration of from about 0.5 μg/mL to about 6 μg/mL, from about 1 μg/mL to about 5 μg/mL, from about 2 μg/mL to about 4 μg/mL.

In some embodiments of the present disclosure, the gold nanoparticle(s) is capped with a material comprising at least one of polyvinylpyrrolidone (PVP), polyethylene glycol (PEG), poly(N-isopropylacrylamide)(PNIPAM), dextran, dimercaptosuccinic acid (DMSA) and combinations thereof. In some embodiments, the AuNP particle(s) comprises at least one PVP capped gold nanoparticle.

In some embodiments of the present disclosure, through the simultaneous optical irradiation and application of an oscillating magnetic field to a nanostructure, cancer cells are destroyed when the nanostructure comprises thermo-responsive nanoparticles comprising cisplatin (CPNP) and the cisplatin releases from the nanoparticles to interact with and destroy the cancer cells.

Thus, in some embodiments of the present disclosure, the CPNP particles comprise multiple shells. In some embodiments, the CPNP particles comprise an inner shell having a diameter of from about 50 nm to about 300 nm and an outer shell having a diameter of from about 50 nm to about 400 nm.

In some embodiments of the present disclosure, the nanostructure(s) comprise at least one CPNP particle at a concentration of from about 50 μg/mL to about 600 μg/mL, from about 100 μg/mL to about 500 μg/mL, or from about 200 μg/mL to about 400 μg/mL.

SEM analysis of synthesized magnetic nanocarriers (CSMNSs) demonstrates the polymer shell. Synthesized magnetic nanocarriers (CSMNSs) exhibited good colloidal stability, strong magnetic properties, and no precipitation after several days. From SEM imaging, slightly oval shaped particles (arising from the surface roughness of the carbon film during sample preparation), were observed. In some embodiments, the mean diameter of the nanocarriers was 268±24 nm. TEM analysis of synthesized magnetic nanocarriers (CSMNSs) demonstrates the distribution of the encapsulated MNPs. Particle encapsulation was assessed by TEM imaging at 120 kV. The resulting TEM micrographs revealed that the magnetic nanocrystals were located near each other, but were separated and did not agglomerate.

An applied field vs. magnetization plot for synthesized magnetic nanocarriers (CSMNSs) at 311 K was conducted, which, demonstrated super-paramagnetic behavior, even at the collapsed state of the polymeric shell. Due to their size and structure, the nanomagnets were expected to exhibit super-paramagnetic behavior at moderate field and frequency (0-150 Oe, 0-1000 kHz) range, which was assessed at 311 K or above the volumetric transition temperature. No hysteresis response was observed, however, even after the volumetric shrinkage of the spheres, which indicated super-paramagnetic behavior and absence of particle agglomeration at elevated temperature.

Figure 2A:
FIG. 2A is an exemplary embodiment of a response of the synthesized magnetic nanocarriers (CSMNSs) to an applied DC magnetic field of 60 Oe by a permanent magnet at the adjacent wall of the flask in accordance with the present disclosure.

FIG. 2A is an exemplary embodiment of a response of the synthesized magnetic nanocarriers (CSMNSs) to an applied DC magnetic field of 60 Oe by a permanent magnet at the adjacent wall of the flask. Under the measured field intensity of 60 Oe, created by a permanent magnet at the adjacent wall of the flask, the CSMNSs moved in the direction of the field and formed a film on the flask wall close to the magnet (FIG. 2A). Almost all particles were completely separated from the solution even with the application of a moderately intense field, which demonstrated their controllability under magnetic field. The CSMNS response to external magnetic field is much stronger than that of the individual magnetic nanodots due to a much higher magnetization value per carrier. Slight agitation brings the nanospheres back into the solution once the magnetic field is removed. This behavior further indicates that the present disclosure is able to trap and maintain these nanocarriers in the targeted tissue regions without being washed away by the blood flow during in vivo applications.

Figure 2B:
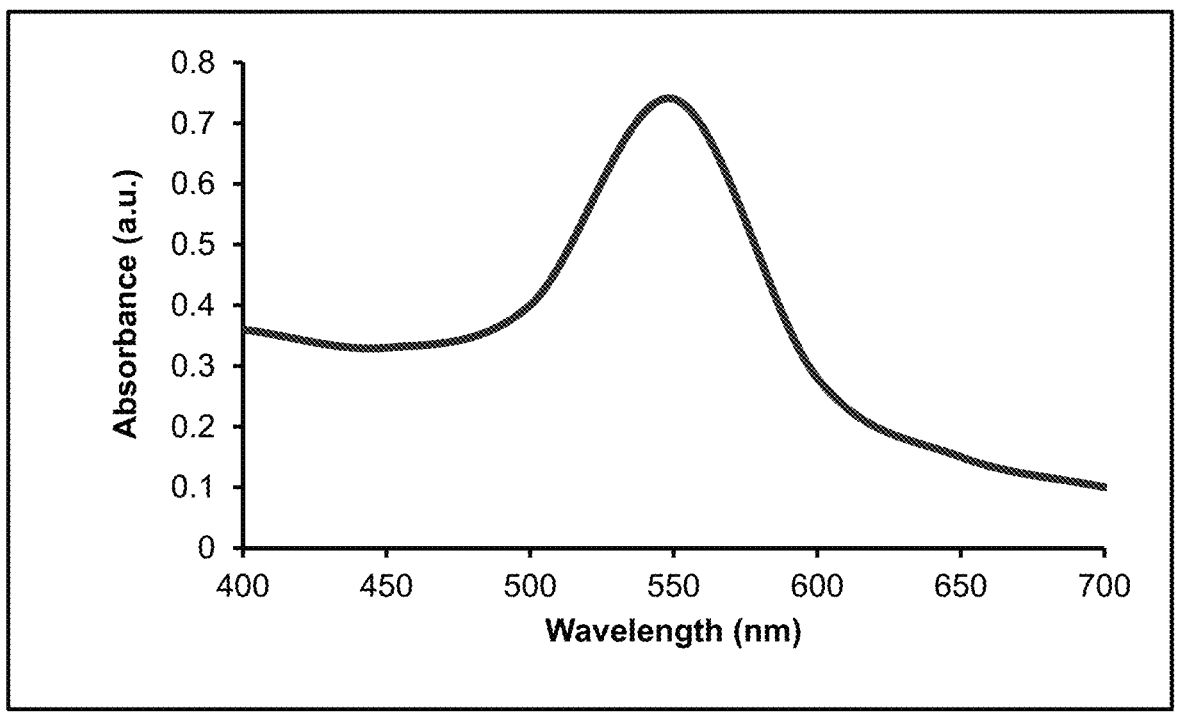
FIG. 2B is an exemplary embodiment of a UV-Vis spectrum of the dispersed AuNPs in the culture media in accordance with the present disclosure.

TEM analysis of the AuNPs demonstrated the particle distribution in cell culture media, ruling out the possibility of agglomeration. FIG. 2B is an exemplary embodiment of a UV-Vis spectrum of the dispersed AuNPs in the culture media. TEM imaging of the AuNPs demonstrated particle distribution in the culture media and the high absorption in the range of 520±15 nm (FIG. 2B) facilitated coupled hyperthermia under hybrid optical-AC magnetic field exposure. The CPNPs comprised two polymer shells with varying degree of hydrophilicity, the inner shell having a diameter of 112±24 nm. Multi-shell nanocarriers expand the volumetric transition range, which in turn facilitates the release of the imbibed therapeutic agents. In some embodiments of the present disclosure, the CPNPs demonstrate monodisperse behavior in the cell culture media. Morphology of the CPNPs was assessed by performing SEM imaging and the mean diameter of the double shell nanocarriers was 191±32 nm.

Figure 2C:
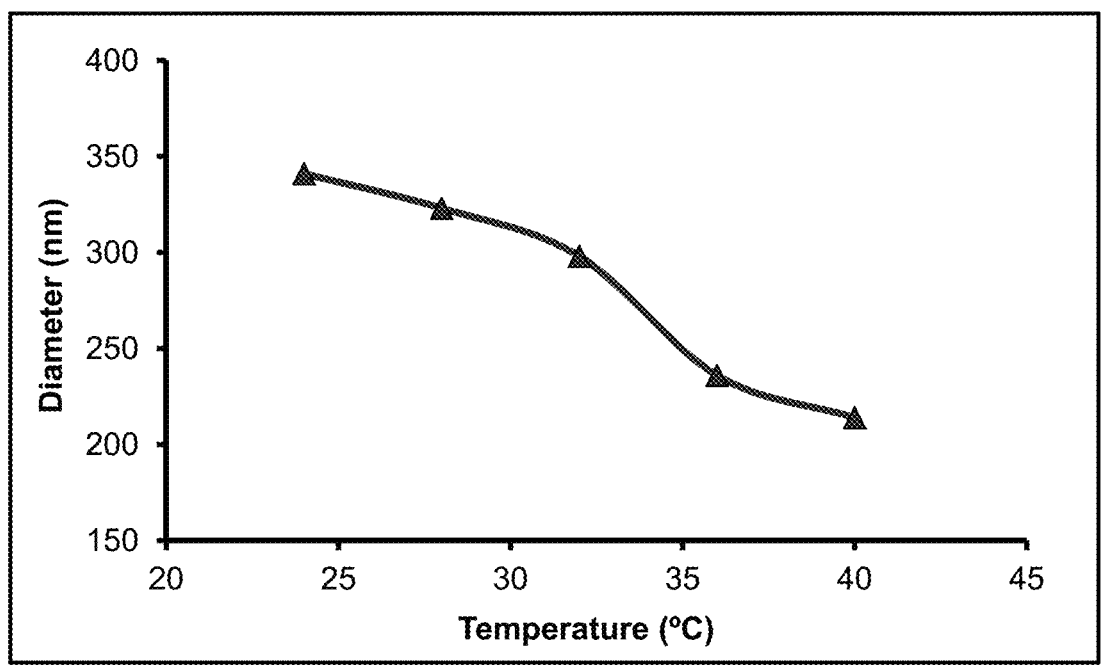
FIG. 2C is an exemplary embodiment of a temperature dependence of hydrodynamic diameter of the CPNPs in accordance with the present disclosure.
Figure 2D:
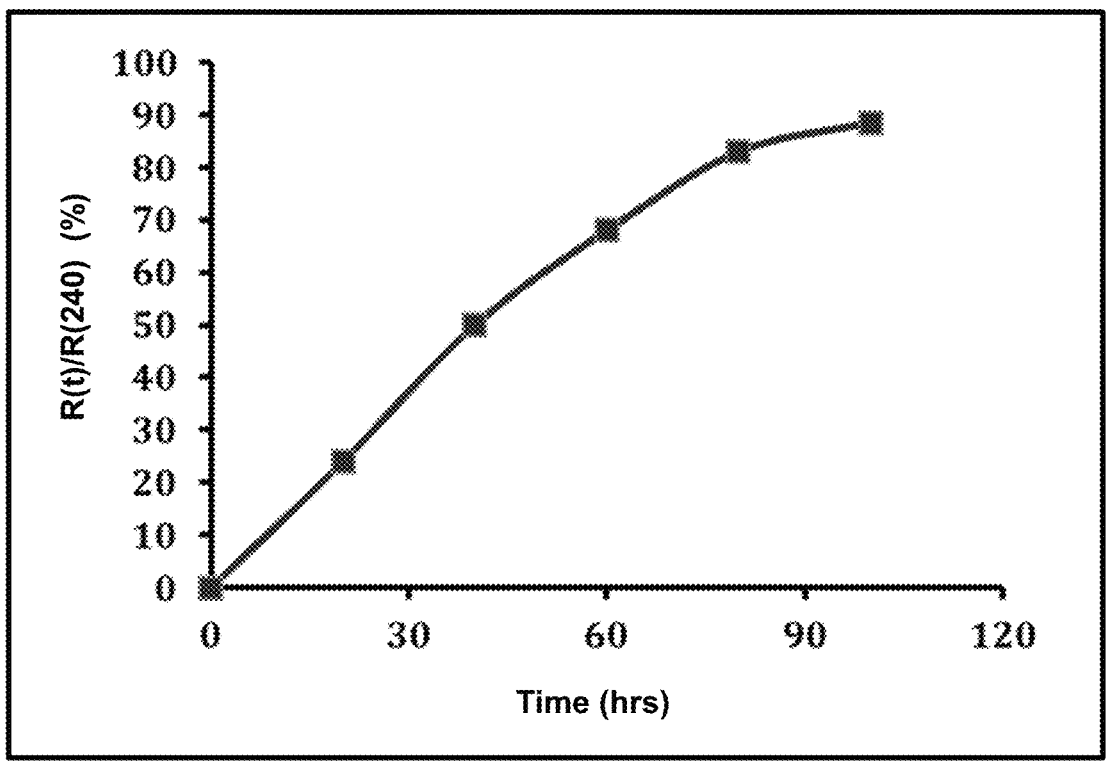
FIG. 2D is an exemplary embodiment of a drug release profile from the CPNPs where R(t) represents mass released at any time t, and R(240) represents total mass released over 240 h (10 days) in accordance with the present disclosure.

FIG. 2C is an exemplary embodiment of temperature dependence of a hydrodynamic diameter of the CPNPs and FIG. 2D is an exemplary embodiment of a drug release profile from the CPNPs where R(t) represents mass released at any time t, and R(240) represents total mass released over 240 h (10 days). The temperature dependent volumetric transition behavior of these cisplatin loaded nanocarriers is shown in FIG. 2C, which demonstrated a broader (31-38° C.) volumetric transition range and consequently, sustained release of the imbibed cisplatin (FIG. 2D).

Figure 3A:
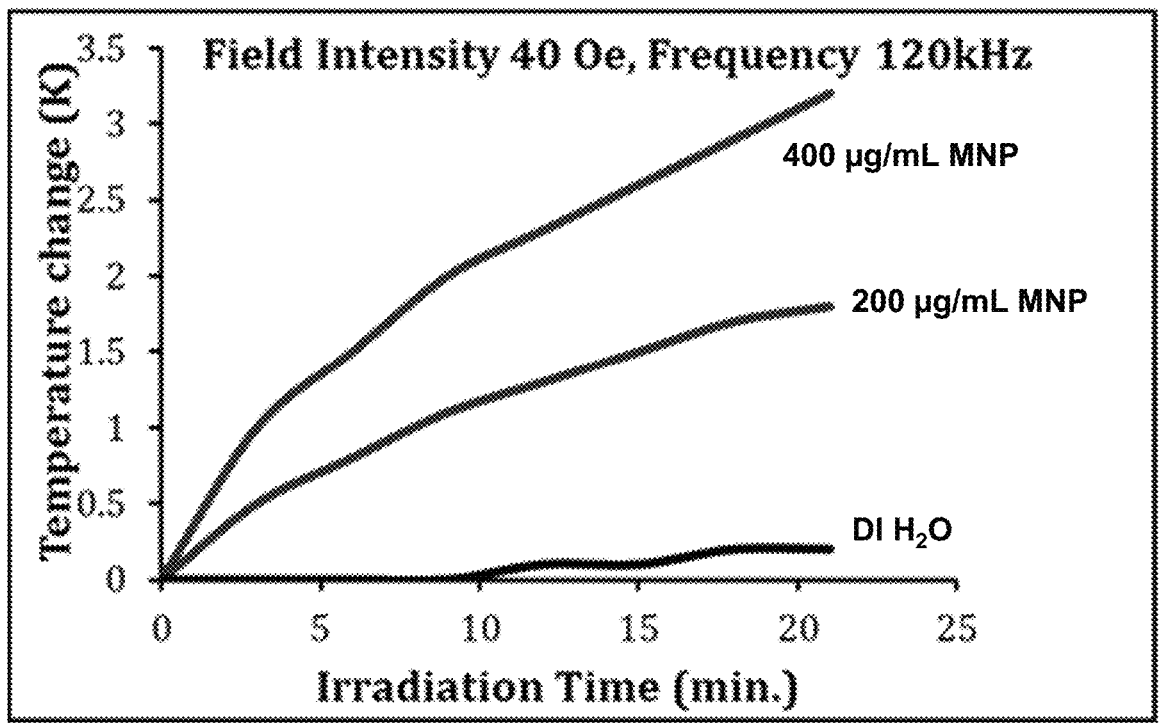
FIG. 3A is an exemplary embodiment of a remote heating response under AC magnetic field exposure as a function of CSMNS concentration at 40 Oe in accordance with the present disclosure.
Figure 3B:
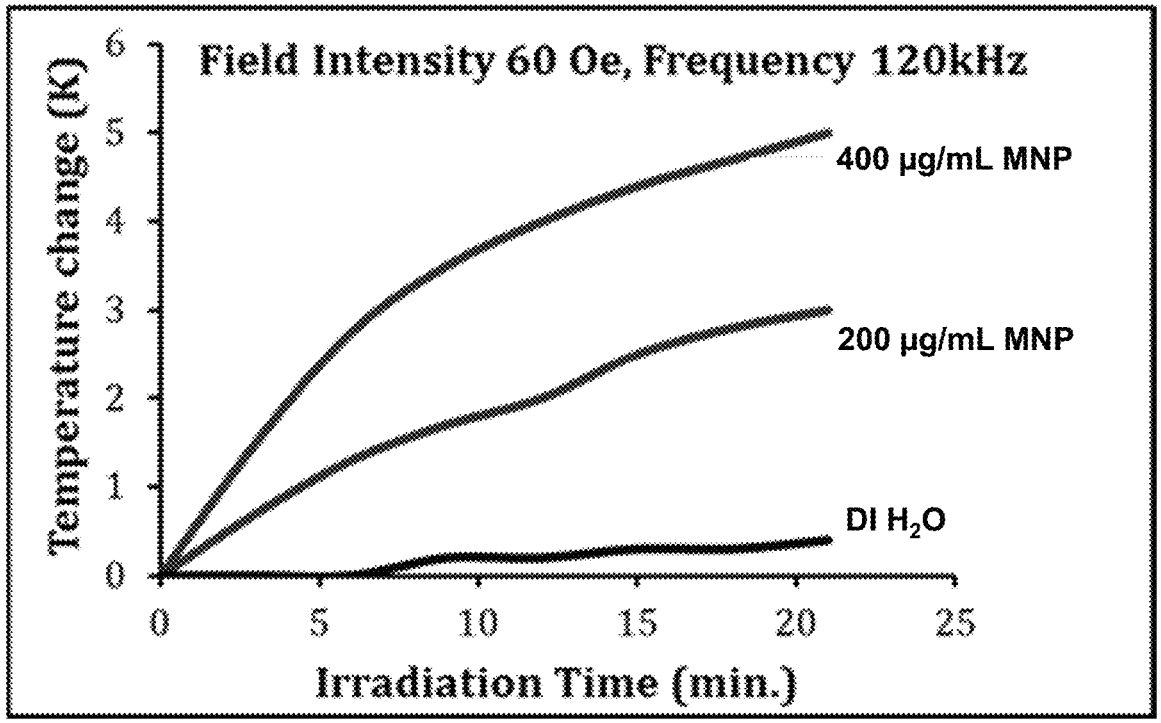
FIG. 3B is an exemplary embodiment of a remote heating response under AC magnetic field exposure as a function of CSMNS concentration at 60 Oe in accordance with the present disclosure.

FIG. 3A is an exemplary embodiment of a remote heating response under AC magnetic field exposure as a function of CSMNS concentration at 40 Oe and FIG. 3B is an exemplary embodiment of a remote heating response under AC magnetic field exposure as a function of CSMNS concentration at 60 Oe. Frequency of the magnetic field was kept at 120 kHz.

Figure 3C:
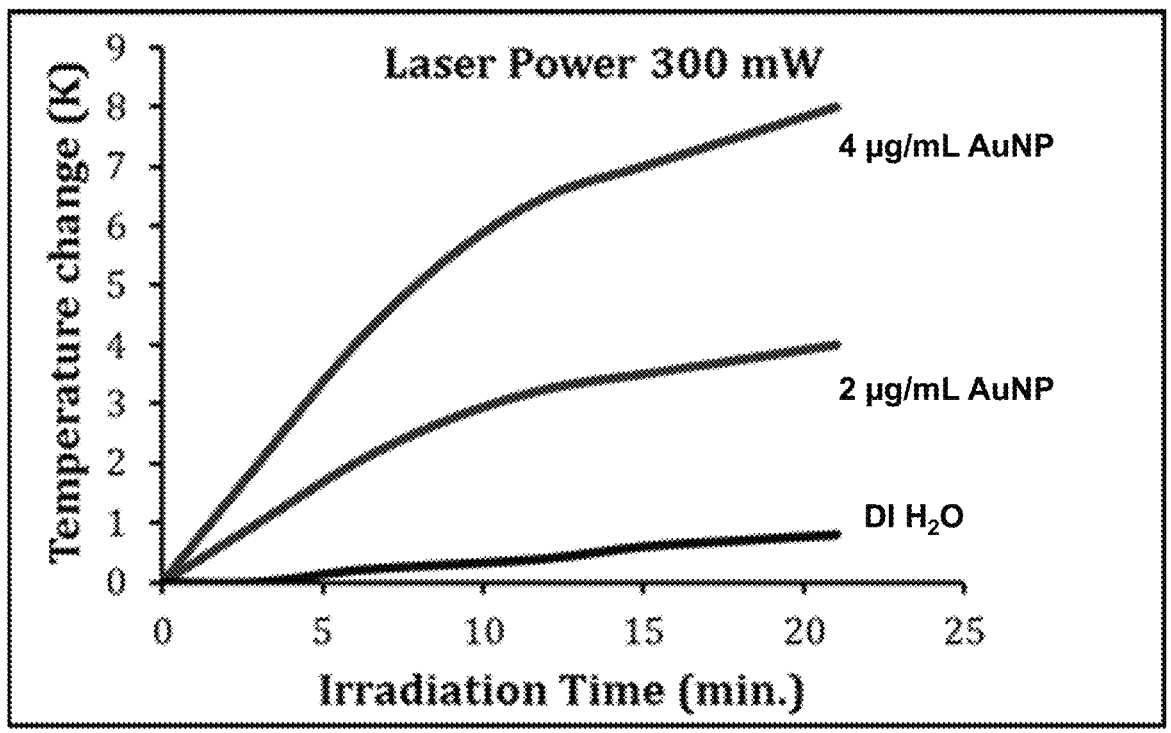
FIG. 3C is an exemplary embodiment of a remote heating response under optical irradiation as a function of AuNP concentration in accordance with the present disclosure.
Figure 3D:
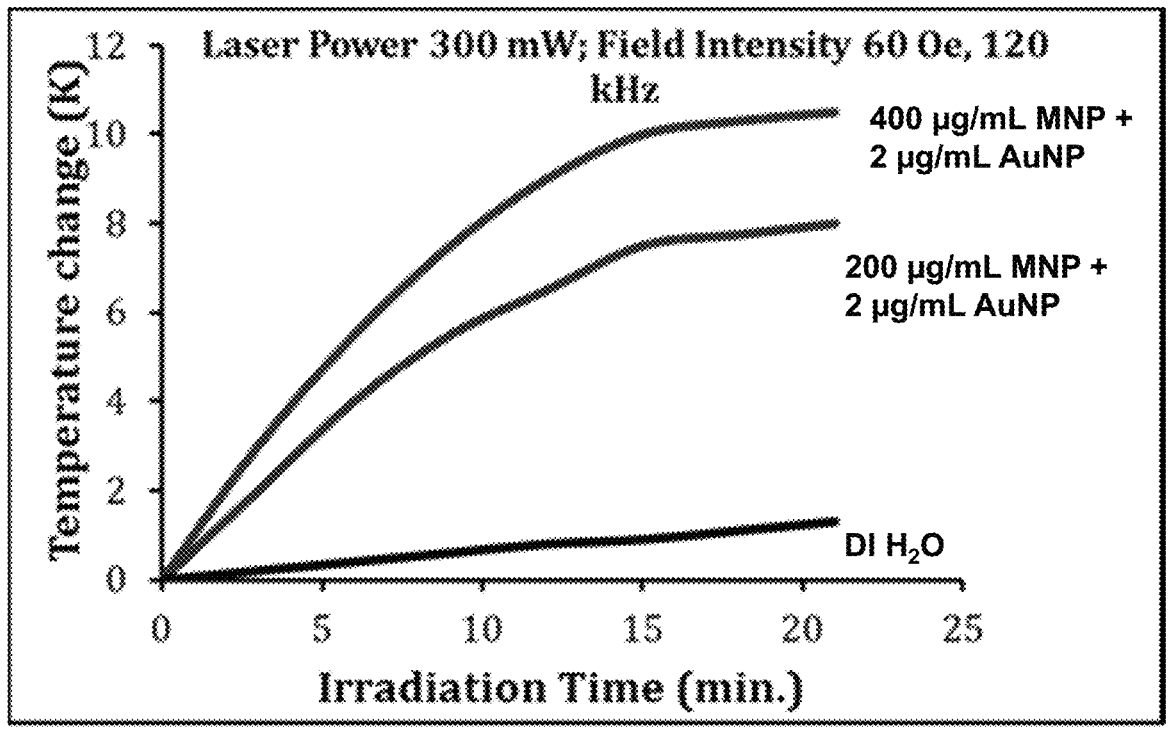
FIG. 3D is an exemplary embodiment of a remote heating response under hybrid optical-AC magnetic field irradiation using CSMNSs and AuNPs together in the media at various concentrations in accordance with the present disclosure.

FIG. 3C is an exemplary embodiment of a remote heating response under optical irradiation as a function of AuNP concentration and FIG. 3D is an exemplary embodiment of a remote heating response under hybrid optical-AC magnetic field irradiation using CSMNSs and AuNPs together in the media at various concentrations. Remote heating response of the nanocarriers was observed under AC magnetic fields (FIGS. 3A and 3B), optical irradiation (FIG. 3C), and under hybrid optical-AC magnetic field exposure (FIG. 3D). Upon field application, the nanocarrier suspended culture media temperature increased in a concentration dependent manner and reached a near steady state after approximately 20-30 minutes of irradiation.

In some embodiments of the present disclosure, the magnetic field has an intensity of from about 0 Oe to about 150 Oe, from about 10 Oe to about 150 Oe, or from about 40 Oe to about 60 Oe. In some embodiments of the present disclosure, the magnetic field has a frequency of from about 0 kHz to about 1000 kHz, from about 50 kHz to about 500 kHz, or from about 60 kHz to about 150 kHz.

In some embodiments of the present disclosure, the laser has a power of from about 100 mW to about 500 mW, from about 200 mW to about 400 mW, or from about 250 mW to about 350 mW.

For AC magnetic field modulation, magnetic nanoparticle (MNP) concentration varied between 200-400 µg/mL, and the temperature change was observed to be in the range of 1.5-3.5 K at 40 Oe, and between 3-5 K at 60 Oe field intensities, respectively. Optical irradiation induced temperature change was in the range of 3.7 K and 8 K respectively, when the concentration of the AuNPs were changed from 2 µg/mL to 4 µg/mL in the culture media. Significantly stronger heating response was observed under the hybrid optical-AC magnetic field, in the range of 8-10.5 K, even with a mixture consisting of only 2 µg/mL AuNPs and 400 µg/mL MNPs. During all measurements, observed joule heating was found to be minimal, in the range of from about 0.5 K to about 1.25 K. In some embodiments, a mixture composition comprises about 400 µg/mL MNPs and about 2 µg/mL AuNPs for executing acute hyperthermia towards the development of a multi modal therapy for the destruction of the neuroblastoma cells.

B35 neuroblastoma cell proliferation was observed post hyperthermia treatments and compared with control (FIG. 4A), and with only nanoparticle exposure (400 µg/mL MNP+2 µg/mL AuNP) in the culture media (FIG. 4B) conditions. The dose levels of the CSMNSs and AuNPs used had very low cytotoxicity, as observed in FIG. 4B and quantified later in FIG. 4I. Hybrid optical and AC magnetic field irradiation did not inhibit cell proliferation in the absence of the nanocarriers, as observed in FIG. 4C, although slight reduction in cell proliferation was observed in the presence of the nanocarriers under separate (i.e. magnetic or optical) actuations (FIGS. 4D-4E). Under combined photo-magnetic actuation in the presence of the nanocarriers, severe inhibition in proliferation with cytoplasmic blebbing and irregularities in shape were observed (FIG. 4F), which even surpassed the culture condition with the 200 µg/mL CPNP exposure in the media (FIG. 4G). Finally, complete ablation of the B35 neuroblastoma cells in culture was observed under photo-magnetic combined actuation in the presence of the magnetic, gold, and the cisplatin loaded nanocarriers (FIG. 4H). AC Magnetic field intensity was 60 Oe, frequency 120 kHz, and laser power 300 mW (520 nm).

Figure 4A:
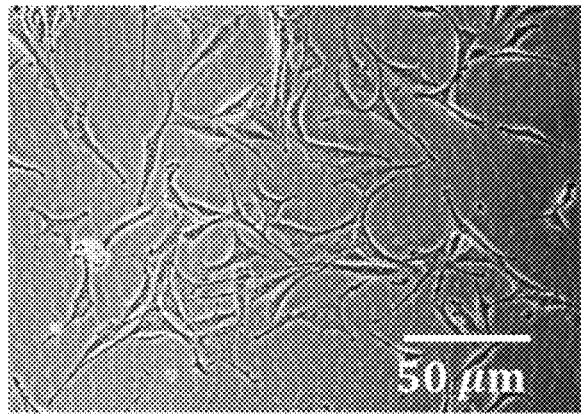
FIG. 4A is an exemplary embodiment of a B35 neuroblastoma cell proliferation under a control in accordance with the present disclosure.
Figure 4B:
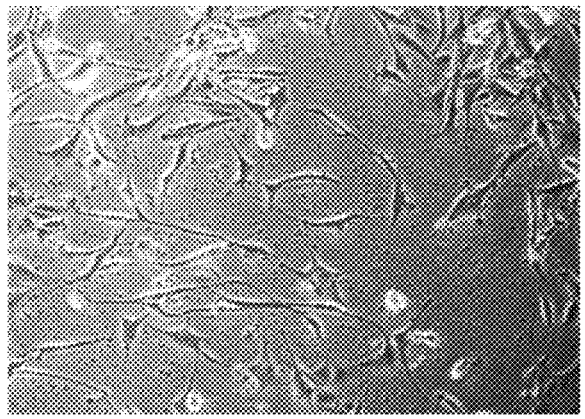
FIG. 4B is an exemplary embodiment of a B35 neuroblastoma cell proliferation under a presence of NPs (400 µg/mL MNP+2 µg/mL AuNP) in the culture media in accordance with the present disclosure.
Figure 4C:
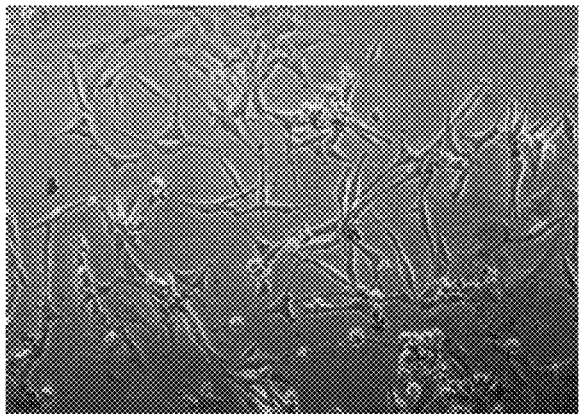
FIG. 4C is an exemplary embodiment of a B35 neuroblastoma cell proliferation under a combined optical-AC magnetic field irradiation in the absence of NPs in accordance with the present disclosure.
Figure 4D:
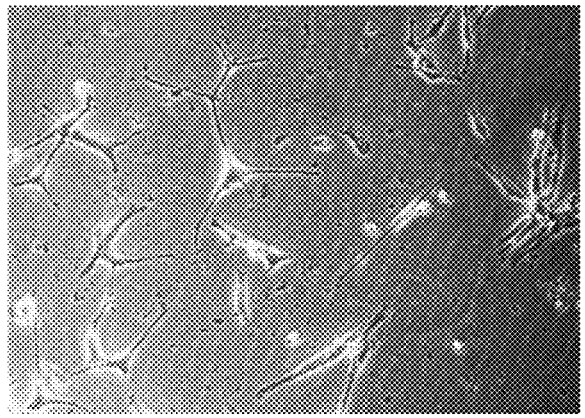
FIG. 4D is an exemplary embodiment of a B35 neuroblastoma cell proliferation under a presence of nanoparticles (NPs) under AC magnetic field irradiation in accordance with the present disclosure.
Figure 4E:
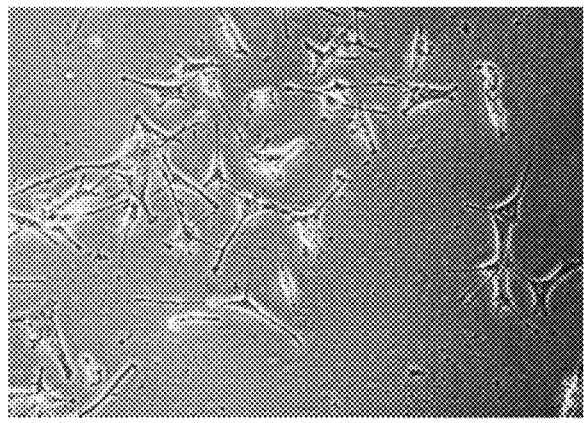
FIG. 4E is an exemplary embodiment of a B35 neuroblastoma cell proliferation under a presence of NPs under optical irradiation in accordance with the present disclosure.
Figure 4F:
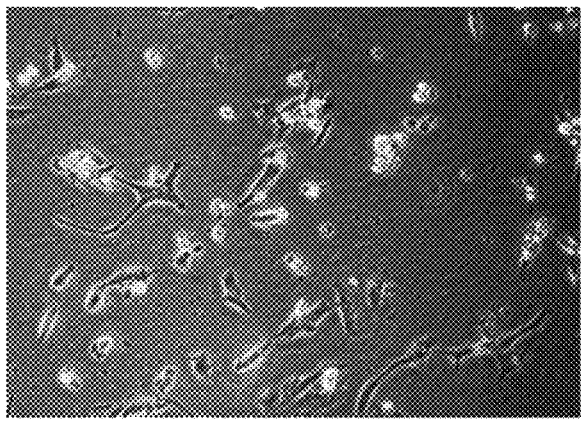
FIG. 4F is an exemplary embodiment of a B35 neuroblastoma cell proliferation under a combined optical-AC magnetic field irradiation in the presence of NPs in accordance with the present disclosure.
Figure 4G:
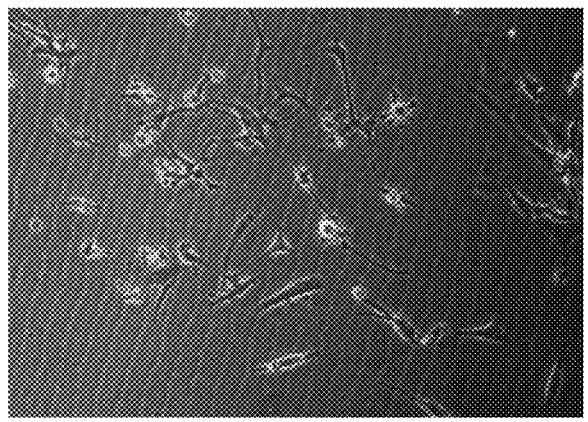
FIG. 4G is an exemplary embodiment of a B35 neuroblastoma cell proliferation under a presence of 200 µg/mL CPNPs in accordance with the present disclosure.
Figure 4H:
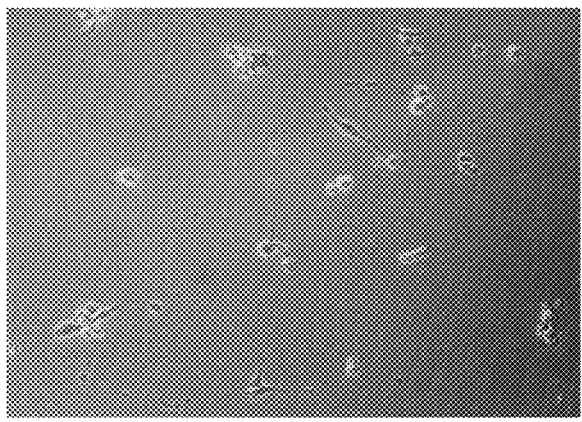
FIG. 4H is an exemplary embodiment of a B35 neuroblastoma cell proliferation under a combined optical-AC magnetic field irradiation in the presence of NPs and CPNPS in accordance with the present disclosure.
Figure 4I:
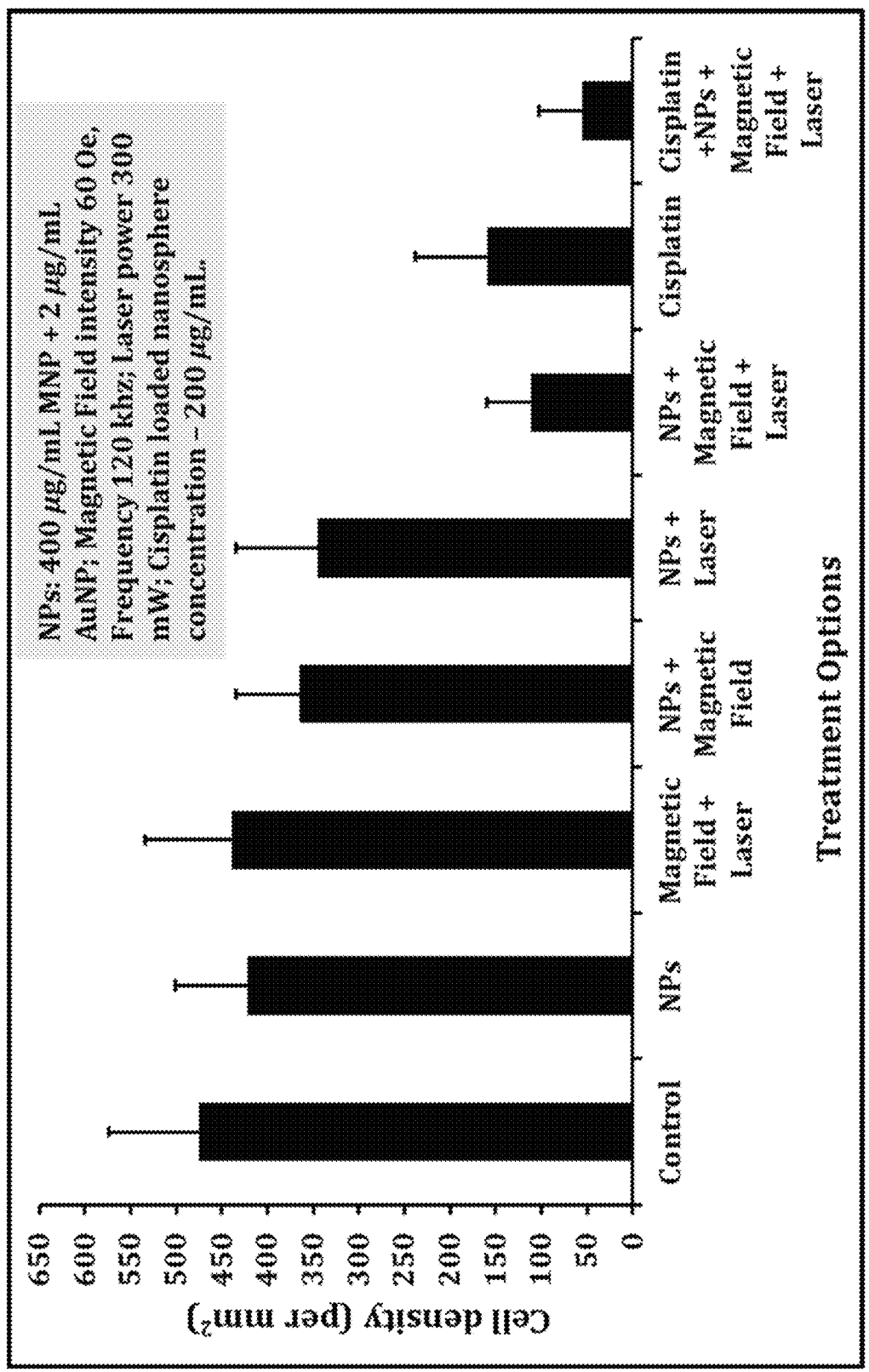
FIG. 4I is an exemplary embodiment of a quantification of average cell densities (cell number/mm$^2$), indicative of cell proliferation for B35 neuroblastoma cells under all treatment options in accordance with the present disclosure.

Scale bar=50 µm in FIG. 4a, and is also applicable for FIGS. 4B-4H. The results of the quantification of average cell densities (cell number/mm2), indicative of cell proliferation for B35 neuroblastoma cells under all treatment options are summarized in FIG. 4I.

Figure 5A:
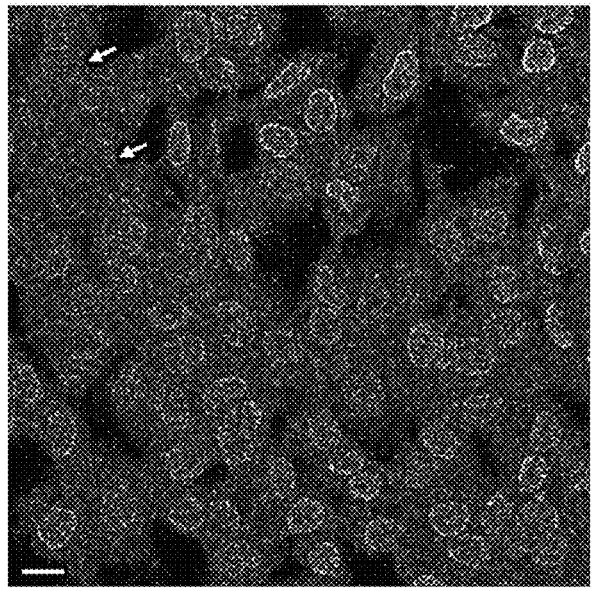
FIG. 5A is an exemplary embodiment of a nuclear condensation and fragmentation under a control in accordance with the present disclosure.
Figure 5B:
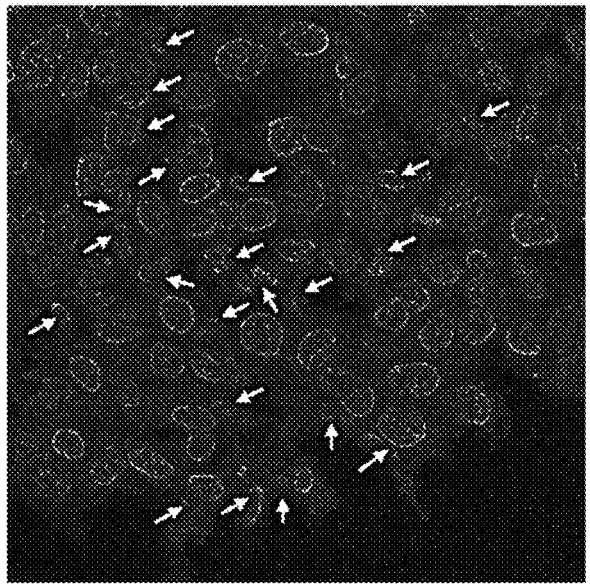
FIG. 5B is an exemplary embodiment of a nuclear condensation and fragmentation under a presence of 200 µg/mL CPNPs in accordance with the present disclosure.
Figure 5C:
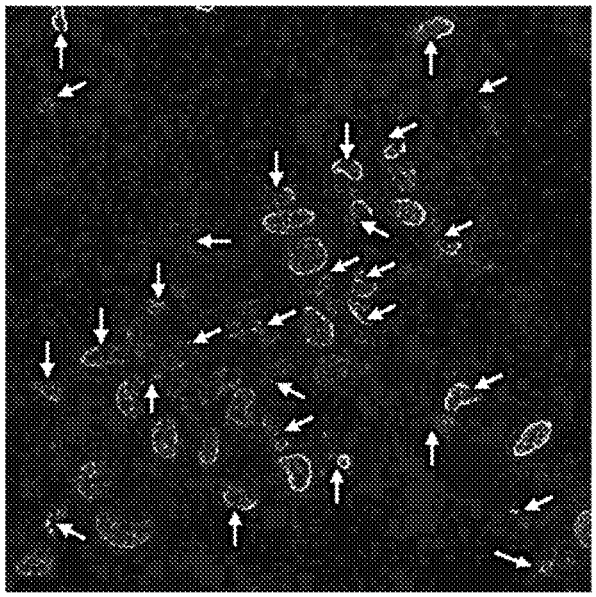
FIG. 5C is an exemplary embodiment of a nuclear condensation and fragmentation under a combined optical-AC magnetic field irradiation in the presence of NPs (400 µg/mL MNP+2 µg/mL AuNP) in accordance with the present disclosure.
Figure 5D:
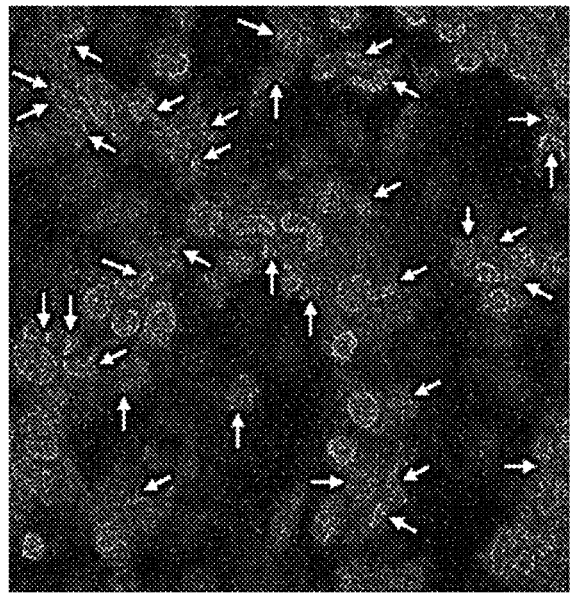
FIG. 5D is an exemplary embodiment of a nuclear condensation and fragmentation under a combined optical-AC magnetic field irradiation in the presence of NPs and CPNPS in accordance with the present disclosure.
Figure 5E:
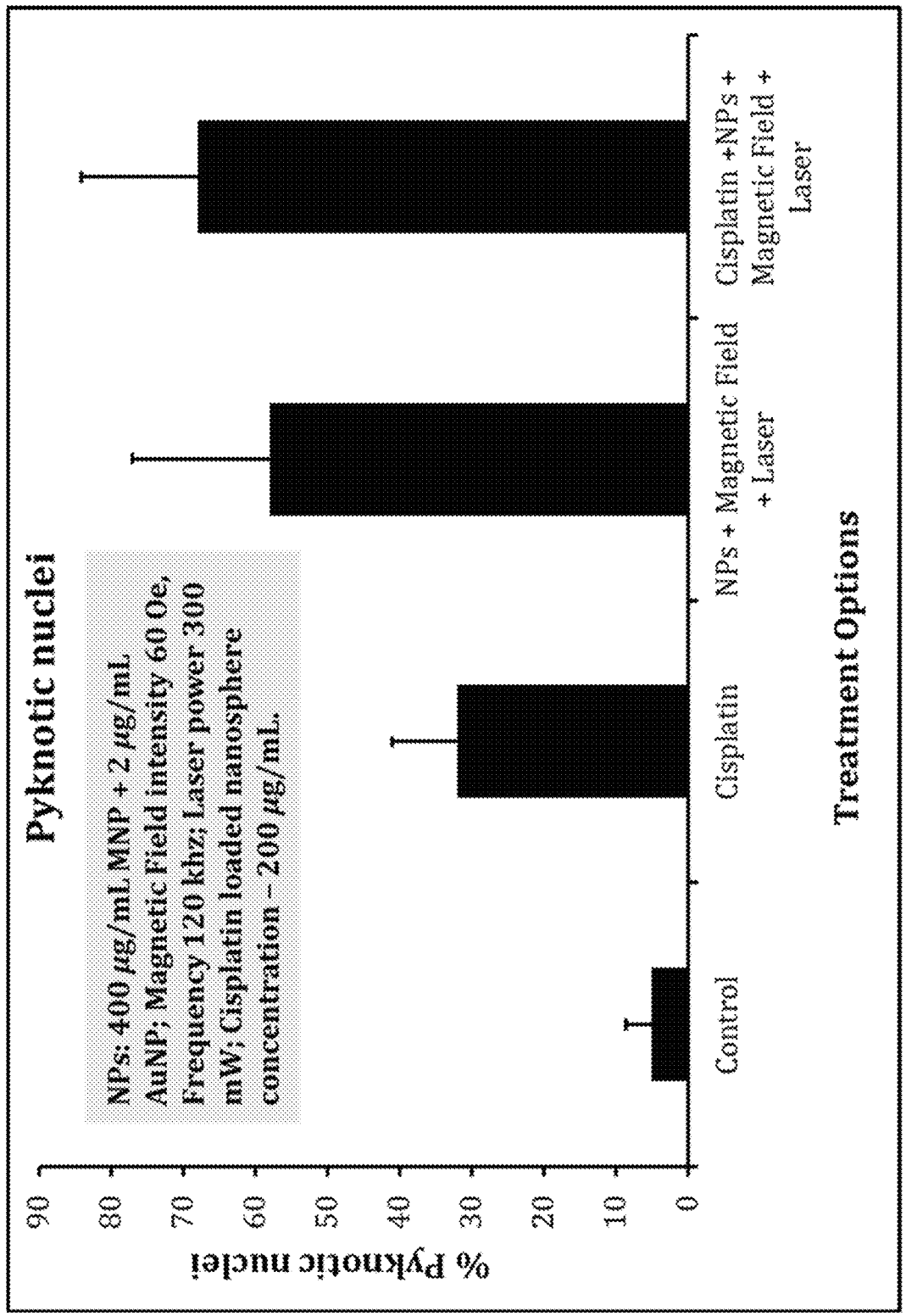
FIG. 5E is an exemplary embodiment of a quantification of pyknotic nuclei, indicative of cell death in accordance with the present disclosure.

Induction of apoptosis was further investigated by observing DAPI stained cell nuclei for the conditions which severely inhibited B35 neuroblastoma cell proliferation as shown in FIGS. 5A-5D. While in control (FIG. 5A), the cells had round and homogeneous nuclei, exposure to CPNPs (200 µg/mL) launched the apoptotic machinery of the cell, as observed from the deformed and condensed nuclei and apoptotic bodies (FIG. 5B). Under combined photo-magnetic actuation in the presence of the gold and magnetic nanocarriers (400 µg/mL MNP+2 µg/mL AuNP), severe chromatin condensation and nuclear fragmentation was evident (FIG. 5C), indicating the potency of photo-magnetic hyperthermia mediated cytotoxicity at a relatively lower irradiation and nanoparticle exposure level. Even a higher degree of damage was observed under photo-magnetic combined actuation in the presence of the CSMNSs, AuNPs, and CPNPs (FIG. 5D), thereby demonstrating the effectiveness of the multimodal therapeutic strategy. AC Magnetic field intensity was 60 Oe, frequency 120 kHz, and laser power 300 mW (520 nm). Scale bar=10 µm in FIG. 5A, and is also applicable for FIG. 5B-5D. Quantification of pyknotic nuclei, which is indicative of cell death, is displayed in FIG. 5E.

Figure 6A:
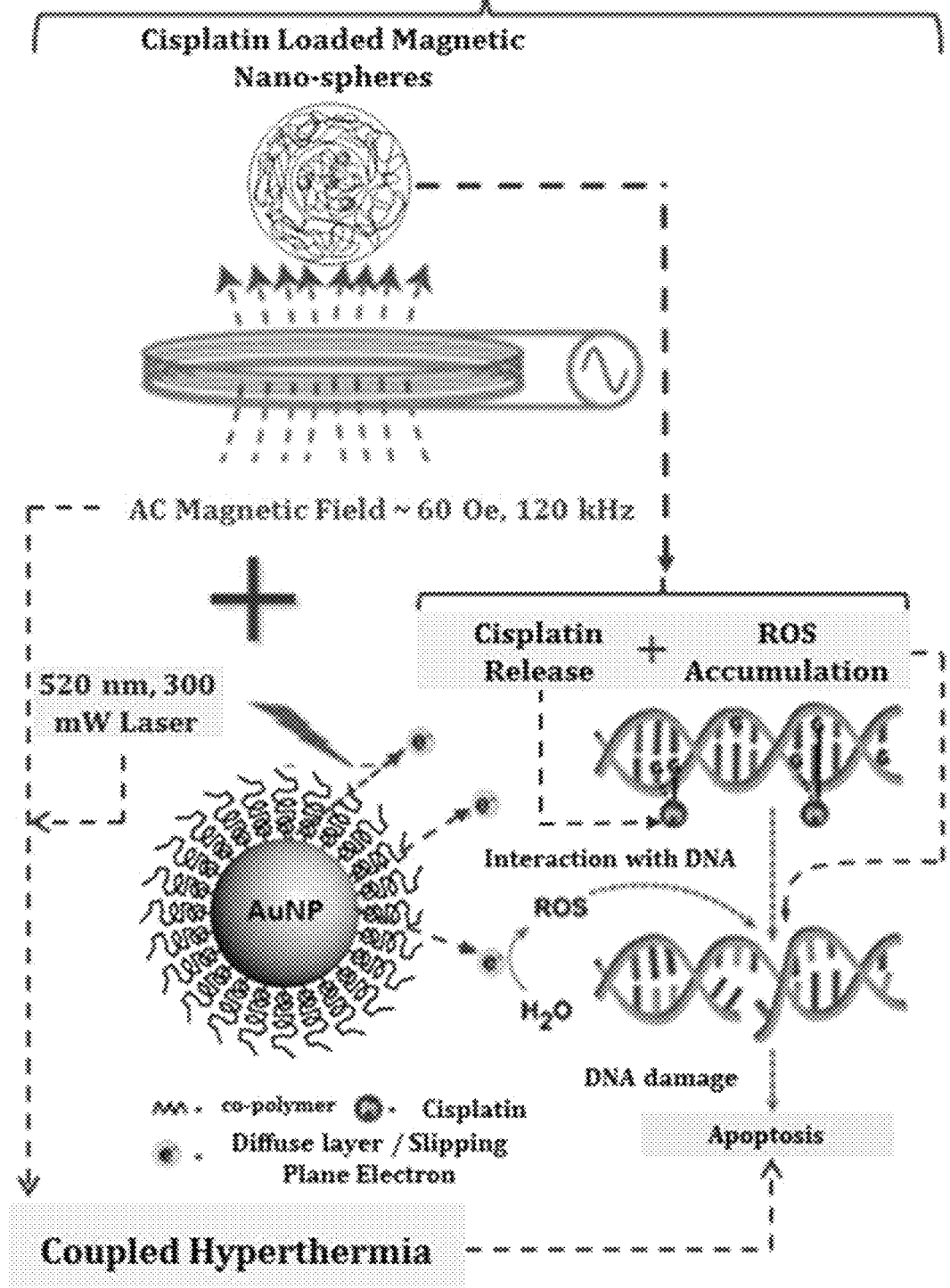
FIG. 6A is an exemplary embodiment of a photo-magnetic stimulation of synergetic nano-carriers for use with an irradiation mediated multi-modal therapeutic strategy of neuroblastoma cells in accordance with the present disclosure.
Figure 6B:
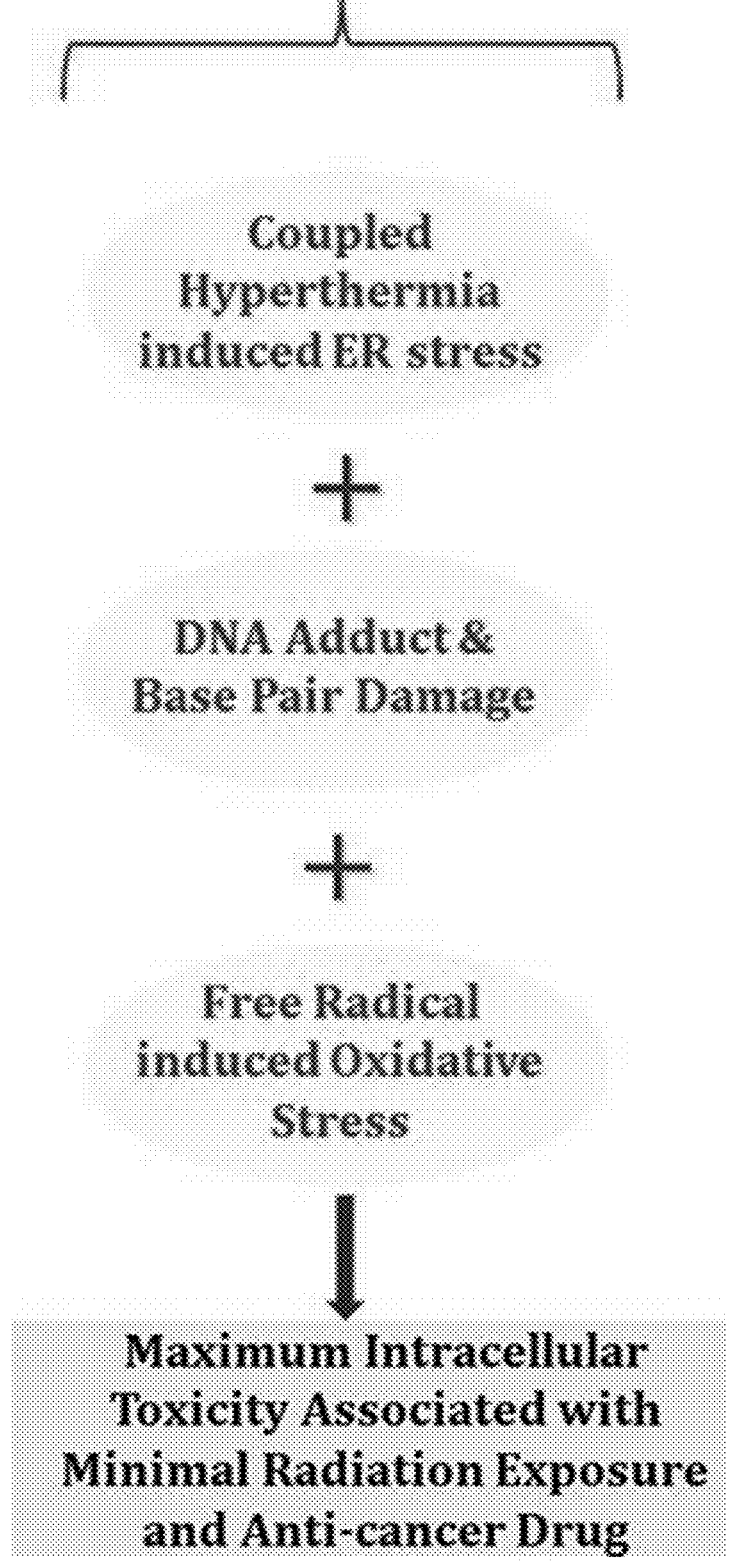
FIG. 6B is an exemplary embodiment of a photo-magnetic irradiation mediated multi-modal therapeutic strategy of neuroblastoma cells using clusters of synergistic nanostructures in accordance with the present disclosure.

In some embodiments of the present disclosure, a photo-magnetic irradiation mediated multimodal therapeutic strategy of neuroblastoma cells using clusters of synergetic nanostructures is disclosed and exemplified in FIGS. 6A and 6B in accordance with the present disclosure. Coupled hyperthermia, DNA damage, and ROS induced apoptosis of B35 neuroblastoma cells in culture was observed. Cisplatin was loaded in a separate non-magnetic nanocarrier. Combined photo-magnetic stimulation was successfully implemented on the cluster of synergetic nanocarriers to develop a multimodal therapy to guide neuroblastoma cell destruction.

Accordingly, in some embodiments, a multimodal therapy includes coupled hyperthermia induced ER stress, DNA adduct and base pair damage, and free radical induced oxidative stress, resulting in maximum intracellular toxicity associated with minimal radiation exposure and anti-cancer drug(s) (see FIGS. 6A and 6B). This strategy permits the use of a less intense AC magnetic field in combination with optical irradiation during the treatment, thus removing the safety concerns associated with the AC magnetic field assisted therapies. Although a green laser (300 mW) was used as the light source for the optical irradiation as a proof of concept, in some embodiments a near infrared (NIR) laser is used to obtain deeper penetration, since the gold nanoparticles can be tuned to possess high NIR absorption. The penetration depth of the optical irradiation is further enhanced by use of a free-space or even fiber-optic Bessel beam, thus eliminating the use of high intensity radiotherapy, which has the potential to incur severe DNA damage and has a risk of developing into a second cancer at a later stage. Moreover, the treatment efficacy was achieved at a reduced nanoparticle dose level. Previously studied nanocarriers were found to be highly non-reactive, stable in physiological solutions, and minimally toxic at even a higher dose level than the dose administered in the present disclosure. Reduced dose level renders them as ideal candidates for photo-magnetic combination therapy.

For tumorigenesis and malignant transformation, responsible molecular mechanisms in accordance with the present disclosure include: (1) over expression of cell survival pathways; and, (2) down regulation of apoptosis. The molecular factors of cell survival pathways include protein kinases (AKT, ALK, P13K, and FAK), transcription factors (NF-ϵ,B, MYCN, and p53), and growth factors (IGF, EGF, PDGF, and VEGF). Manipulation of cell survival pathways reduces the malignant potential of the tumor; which, in turn, provides reduction of dosages and dose related side effects of the conventional therapies in clinical practice. Moreover, since the presence of residual cancer cells in the hematopoietic compartment is the plausible explanation for tumor relapse, highly sensitive methods to detect and isolate rare circulating tumor cells can lead to improved treatment efficacy. In the present disclosure, the cluster of nanostructures used carries the potential to act as an effective modulator of these pathways and selectively targets the tumor cells due to their controllability under hybrid photo-magnetic field and temperature-sensitive behavior. Temperature dependent hydrophilic-hydrophobic transition behavior renders them suitable for drug delivery applications as well, in which triggered release is necessary.

Kinases are enzymes to phosphorylate; thus they act as on-off switches for activating other factors in cell signaling pathways. AKTkinase regulates important cellular functions like cell growth, proliferation, survival, and angiogenesis. In human tissue samples, the AKT phosphorylation was more prevalent in primary neuroblastoma then in benign ganglioma or in normal adrenal tissue. Down regulation of AKT to increase apoptosis is one of the many ways to address the neuroblastoma tumor growth, and two different strategies are: (1) long-term exposure of SH-SY5Y cells to interferonβ, which decreased activation of P13K-AKT pathway, thereby increasing the apoptosis; and (2) Rapamycin induced mTOR (a downstream effector of AKT) inhibition, which is related with decreased tumor growth, angiogenesis, and increased apoptosis. Similarly, inhibition of FAK by siRNA or small molecule inhibitors, such as NVP-TAE 226 and Y15 results in decreased cell survival, increased apoptosis, and G2 cell cycle arrest. NVP-TAE 226 (Mol. Wt. 468.94) and Y15 (Mol. Wt. 284.01) are ideal to be loaded into these designed nanocarriers due to their low molecular weight and adequate water solubility, which will be extremely beneficial for controlled release into the tumor cells under photo-magnetic stimulation. Among transcription factors, NF-κB has important roles in neuroblastoma chemo resistance as doxorubicin and VP16 have both shown to trigger NF-κB activation in neuroblastoma cells, inhibiting apoptosis; nevertheless, siMYCN (siRNA against MYCN) has been found to increase caspase-3 mediated apoptosis. Selective inhibition of MYCN is achieved using an anti-gene peptide nucleic acid (PNA), which can either be covalently attached to the nanocarrier surface, or was loaded inside for on-demand release when the target site is reached. Targeted therapy to modulate the growth factors is another direction for the treatment of high risk neuroblastoma. Certain tyrosine kinase inhibitors of PDGFR (PDGF receptor) have shown to inhibit the growth of a number of human neuroblastoma cell line in vitro and xenograft in vivo. Nanocarrier mediated neurite growth factor (NGF) delivery to neuronal model cells for promoting neurite outgrowth has been shown. In some embodiments, a similar strategy is used for the delivery of selected growth factor mediated cell survival pathway modulators to the targeted cancer cells.

For high risk neuroblastoma treatment, identifying and targeting the rare circulating tumor cells or removal of the nucleic acids from such cells is extremely important to prevent the tumor relapse. Förster resonance energy transfer (FRET) based multifunctional nanocarriers were designed, which are capable of performing organelle specific binding for detection of damaged cells and can provide on-demand release of a specific drug or a combination of drugs. Combined with the photo-magnetic actuation, in some embodiments these nanocarriers perform detection at the single cell level, which leads to a greater understanding of how to handle residual tumor cells. Further, since most of these aforementioned tasks can be performed with various types of magnetically controllable nanocarriers, in some embodiments diffusion out of the targeted area is prevented using a concentrated DC magnetic field during in vivo localization. Use of a Halbach cylinder extends the penetration depth of the applied magnetic field during clinical applications.

EXAMPLE

Photo-Magnetic Actuator Design

In accordance with the present disclosure, a unique photo-magnetic actuator was designed to perform simultaneous optical and AC magnetic field stimulation of cultured mammalian cells or dispersed nanocarrier systems (FIGS. 1A and 1B). The incubator 8 consists of a sample chamber 9 for placing TPP tissue culture tubes, AC/DC magnetic field generating coil 10, a cage 12 for placement of LEDs for low level optical irradiation, and a high performance glass window at the front wall of the incubator for transmitting the laser irradiation path 11 during moderate/high level optical stimulation. Inside the sample chamber 9, the B35 neuroblastoma cells were cultured or the nanocarriers were colloidally dispersed, as needed. The circuit utilized a capacitor bank in series with the inductor coil and a $0.5\Omega$ resistor. Magnetic field in the range of 10-150 Oe, 60-150 kHz was produced, as needed by changing the capacitor and/or the coil inductance. A temperature controlling unit/heating element 7 was attached to stabilize the incubator temperature in the range of 36-37° C. during the experiments, and the top and the bottom panels of the incubator 8 were designed to be removable to allow easy swapping of the samples. The incubator 8 was attached to the base of the class 3B laser 2 (520 nm, 300 mW), and a laser stop 4 was placed to the rear of the incubator 8 to inhibit reflection. Further, black absorbent tape material was used to confine the laser 2 exposure to only necessary areas. A fiber optic thermometer 5 was used to measure precise temperature change during heating of the nanocarriers. The electronics (e.g., 5,6,7) and the laser systems (e.g., 2,3,4) were mounted at a safe distance from the incubator to rule-out possible interference that creates fluctuations of the AC magnetic field intensity during measurements.

Nanocarrier Design

Magnetite ($Fe_3O_4$) core-polymeric shell nanospheres (CSMNS) were synthesized. A thermo-activated polymer network of poly(ethylene glycol) ethyl ether methacrylate-co-poly(ethylene glycol) methyl ether methacrylate (PEGEEMA-co-PEGMEMA) was synthesized first using a precipitation polymerization method. Specifically, 2.1 g of PEGEEMA ($M_n$~246 g mol$^{-1}$, Aldrich), 0.69 g PEGMEMA ($M_n$~300 g mol$^{-1}$, Aldrich), 0.08 g of acrylic acid (AA), sodium dodecyl sulfate (SDS, 0.02 g) surfactant, and 0.06 g of ethylene glycol dimethacrylate (EGDMA, 97%, Fluka) were dissolved in 150 mL of DI water. The solution was purged with nitrogen gas for 40 minutes at 70° C. Ammonium persulfate (APS, 0.07 g), dissolved in 5 mL of water, was added to initiate the emulsion copolymerization. The reaction lasted for 6 hours under a bubbling nitrogen gas atmosphere. The nanospheres were purified via a dialysis tube (MW cut-off 13,000) against water for 7 days at room temperature with DI water exchanged twice daily. The membrane pore size allowed only the surfactant, SDS, to pass out into the surrounding water while keeping the polymer encapsulated magnetic nanospheres in the solution within the dialysis tubing. The outer shell prepolymer solution was prepared by dissolving 2.4 g of PEGEEMA, 1.61 g PEGMEMA, 0.15 g of AA, and 0.08 g of EGDMA (97%, Fluka) in 150 mL of DI water. The solution was purged with nitrogen gas for 40 minutes. Previously synthesized nanosphere dispersion (150 mL) was put into a reactor and heated up to 70° C. under a nitrogen environment for 40 minutes. Then the outer shell solution was dripped into the reactor, which took about 45 minutes to finish the process. APS (0.07 g) dissolved in 5 mL of water was added to initiate the emulsion copolymerization. The reaction lasted for 6 hours under a bubbling nitrogen gas atmosphere (70° C.). The nanospheres were purified as stated before. At this point, one batch of these designed spheres was used to synthesize magnetic nanocarriers, while the other batch was freeze dried and later used to load the anticancer drug cisplatin (Sigma Aldrich), as described below. Polyvinylpyrrolidone (PVP) capped gold nanoparticles (0.05 mg/mL, 5 nm diameter) were obtained.

After formation of the double-shell particles and repeated washing cycles, 315 mg of $FeCl_3.6(H_2O)$ dissolved in 10 mL of DI water and 125 mg of freshly prepared $FeCl_2.4(H_2O)$ aqueous solution was added to the nanosphere dispersion (300 mL). The solution was purged with nitrogen gas for 24 hours at room temperature. AA was used to take-up the iron ions. Moreover, the addition of PAA increased the pH value. As the pH value increased, the PAA became ionized to make the nanospheres swell more in water, thus uptake of the iron ion was increased. At this point, double shell nanospheres consisting of ferrous and ferric ions were collected by ultracentrifugation and re-suspended in distilled water. While being rapidly stirred, the above acidic solution was neutralized by the drop-wise addition of cooled (4° C.) 28-30% $NH_4OH$ solution. Complete precipitation of $Fe_3O_4$ was observed at a pH of ~12. As acrylic acid was added during the outer shell synthesis, some iron ions were expected to remain at the very outer surface of the nanospheres, which subsequently form $Fe_3O_4$ nanocrystals during the precipitation process. To remove the outer surface attached nanomagnets or excess nanocrystals formed inside the reaction solution during the co-precipitation process, the spheres were repeatedly washed by repeating the cycle of re-dispersion and centrifugation (three to four times, 7000 rpm). The nanospheres were purified as previously stated.

Loading the Drugs in Polymeric Nanocarriers and Characterization of Release Profile Aqueous solution of cisplatin (2 mg/ml) was added to the previously prepared freeze-dried (non-magnetic) nanospheres. The solution was stirred for 24 h at room temperature and the cisplatin loaded nanoparticles (CPNPs) were collected by centrifugation. A specialized diffusion chamber (PermeGear Static Franz cell) with two compartments was used for in vitro release kinetics measurement. The two compartments communicated through an opening of 2 cm diameter. A semipermeable membrane (MW cut-off 13,000 Da) was used to cover the opening. CPNP solution was placed in the donor compartment and the receiver compartment was filled with the DI water. To determine the concentration of released cisplatin (at room temperature and at 37° C.) in the receiving compartment, samples were withdrawn at definite time intervals (20, 40, 60, 80 and 100 h) and the absorbance was measured by UV-VIS Spectroscopy at a wavelength of 301 nm.

Scanning and Transmission Electron Microscopy

Sphere morphology was assessed using an FEI NOVA 230 NANOSEM Scanning Electron Microscope (SEM). Cryo-immobilization was performed to prevent the nanospheres from collapsing during electron microscopy. Accelerating voltages during SEM imaging were kept between 5-20 kV. Before imaging, nanocarriers were sputter coated with an approximately 20-nm thick coating of an Au-Pd alloy in a Gatan 682 Precision Etching Coating System (PECS). Encapsulated magnetic nanodots were observed using a Philips EM 420 Transmission Electron Microscope (TEM, 120 kV electron beam).

Light Scattering and Magnetic Measurements

Dynamic light scattering (DLS) measurements were performed to examine the volumetric transition behavior using a Malvern NanoZS system equipped with a Helium-Neon laser (632.8 nm) as the light source. The hydrodynamic radius distribution of the nanospheres in water was measured at a scattering angle of 60°. Magnetic property [M(H)] of the nanospheres was measured using a Lakeshore model 7300 Vibrating Sample Magnetometer (VSM) at ambient temperature and at 38° C.

Cell Culture and Treatment

B35 rat neuroblastoma cells (ATCC, Manassas, Va.) were routinely cultured at 37° C. in 5% $CO_2$ and 85% relative humidity by using Dulbecco's modified Eagle's medium (DMEM, Invitrogen, Carlsbad, Calif.) derived complete media which contains 90% DMEM, and 10% FBS. For the experiments, about 10,000 cells were seeded in TPP tissue culture tube flasks (10 $cm^2$ growth surface area) containing 2 ml of DMEM complete media and were allowed to grow for 48 hours or more until 70% confluence were observed. All the experiments were performed in triplicates.

For the treatment with nanoparticles, after 48 hours of cell growth and attachment, the cells were washed with serum free DMEM and were exposed to the NPs (various concentrations of MNPs and/or AuNPs), which were colloidally suspended in the culture media. During nanoparticle exposure, cultures were placed into serum free DMEM to prevent particle aggregation. After 4 hours of exposure, the cells were washed with serum free DMEM and were cultured back into 2 ml complete DMEM media until the beginning of the next exposure cycle. The treatment was repeated thrice for every 24 hours. At the end of the final exposure, live cell imaging was performed to assess cell proliferation.

For AC magnetic field exposure, optical irradiation, and hybrid optical-AC magnetic field exposure, the cells were cultured and exposed to the NPs as mentioned earlier. Immediately after the addition of NPs (MNPs and/or AuNPs), the cells were exposed to AC magnetic field exposure/optical irradiation/hybrid optical-AC magnetic field exposure [magnetic field intensity 60 Oe, frequency 120 kHz, laser power 300 mW] for 15 minutes. Following irradiation, the cells were placed in the incubator for 3 hours and 45 minutes as part of the treatment. After 4 hours of NP exposure and irradiation, the cells were washed with serum free DMEM and were cultured back into 2 ml complete DMEM media until the beginning of the next exposure cycle. The treatment was repeated thrice for every 24 hours. At the end of the final exposure, live cell imaging was performed to assess cell proliferation.

For the treatment with cisplatin loaded thermo-responsive nanoparticles (CPNPs), after 48 hours of cell growth and attachment, the cells were washed with serum free DMEM and were exposed to the CPNPs (200 μg/mL), which were colloidally suspended in the culture media for 4 hours. After 4 hours of exposure, the cells were washed with serum free DMEM and were cultured back into 2 ml complete DMEM media until the beginning of the next exposure cycle. The treatment was repeated thrice for every 24 hours. At the end of the final exposure, live cell imaging was performed to assess cell proliferation.

For hybrid optical-AC magnetic field exposure in the presence of CPNPs, the cells were treated (with CPNPs) as mentioned earlier. After the addition of the CPNPs, the cells were exposed to hybrid optical-AC magnetic field exposure [magnetic field intensity 60 Oe, frequency 120 kHz, laser power 300 mW] for 15 minutes. Following irradiation, the cells were placed in the incubator for 3 hours and 45 minutes as part of the treatment. After 4 hours of CPNP exposure and irradiation, the cells were washed with serum free DMEM and were cultured back into 2 ml complete DMEM media until the beginning of the next exposure cycle. The treatment was repeated thrice for every 24 hours. At the end of the final exposure, live cell imaging was performed to assess cell proliferation.

Nuclear morphology was assessed using confocal images captured through a 64X objective from cells (cultured on the coverglasses, which were inserted into the TPP tissue culture tube flasks and fixed) labeled with 4', 6-diamidino-2-phenylindole (DAPI, Ex=405 nm, Em=450/35 nm), following various treatments.

Optical and AC magnetic field assisted therapeutic strategy for high risk neuroblastoma treatment was developed. Synergetic nanostructures CSMNSs, AuNPs, and CPNPs at a reduced dose level were used to create coupled hyperthermia and induce sustained release of the imbibed cisplatin, which caused complete ablation of the B35 neuroblastoma cells. This enabled replacement of high energy x-ray and high intensity AC magnetic field exposure. The developed technique has the potential to combine the modulation of cell survival pathways and the detection of rare circulating tumor cells, which can lead to a greater understanding and comprehensive solution to overcome the existing challenges to treat high risk neuroblastoma. The results show that photo-magnetic irradiation based multimodal therapy is a viable approach to remotely guide neuroblastoma cell destruction and the technique can be extended to treat other aggressive cancers.

What is claimed is:

1. A nanostructure for cancer cell destruction, the nanostructure comprising:
   a cluster of nanoparticles comprising:
      at least one core-shell magnetic nanosphere (CSMNS) nanoparticle, at least one capped gold nanoparticle (AuNP), and at least one a cisplatin loaded thermo-responsive polymeric nanoparticle (CPNP), wherein the cisplatin is loaded inside the CPNP.

2. The nanostructure of claim 1, wherein the at least one CPNP comprises multiple shells.

3. The nanostructure of claim 1, wherein the at least one capped AuNP is capped with a material comprising at least one of polyvinylpyrrolidone (PVP), polyethylene glycol (PEG), poly(N-isopropylacrylamide) (PNIPAM), dextran, dimercaptosuccinic acid (DMSA) and combinations thereof.

4. The nanostructure of claim 1, wherein the at least one CSMNS nanoparticle has a diameter of from 50 nm to 400 nm.

5. The nanostructure of claim 1, wherein the at least one CPNP comprises an inner shell and an outer shell, the inner shell having a diameter of from 50 nm to 300 nm and the outer shell having a diameter of from 50 nm to 400 nm.

6. A multimodal method of cancer cell destruction, the method comprising:

applying optical irradiation induced temperature change to at least one nanostructure comprising a cluster of nanoparticles;

simultaneously applying an oscillating magnetic field to the at least one nanostructure, wherein the cluster of nanoparticles comprises at least one core-shell magnetic nanosphere (CSMNS) nanoparticle, at least one capped gold nanoparticle (AuNP), and at least one thermo-responsive polymeric nanoparticle comprising cisplatin (CPNP), and wherein the simultaneous optical irradiation induced temperature change and oscillating magnetic field application creates a sustained release of the cisplatin from the CPNP; and, interacting the released cisplatin with at least one cancer cell to destroy the cell.

7. The method of claim 6, wherein the simultaneous irradiation and application of the oscillating magnetic field occur with an incubator-actuator device.

8. The method of claim 6, wherein the magnetic field has an intensity of from 0 Oe to 150 Oe.

9. The method of claim 6, wherein the magnetic field has a frequency of from 0 kHz to 1,000 kHz.

10. The method of claim 6, wherein the nanostructure comprises the at least one CPNP at a concentration of from 50 μg/ml to 600 μg/ml.

11. The method of claim 6, wherein the at least one CPNP comprises multiple shells.

* * * * *